US008273575B2

(12) United States Patent
Goodenowe

(10) Patent No.: US 8,273,575 B2
(45) Date of Patent: Sep. 25, 2012

(54) METHODS FOR THE DIAGNOSIS, RISK ASSESSMENT, AND MONITORING OF AUTISM SPECTRUM DISORDERS

(75) Inventor: Dayan Goodenowe, Saskatoon (CA)

(73) Assignee: Phenomenome Discoveries Inc., Saskatoon, Saskatchewan (CA)

( * ) Notice: Subject to any disclaimer, the term of this patent is extended or adjusted under 35 U.S.C. 154(b) by 55 days.

(21) Appl. No.: 12/670,426

(22) PCT Filed: Jul. 25, 2008

(86) PCT No.: PCT/CA2008/001366
§ 371 (c)(1),
(2), (4) Date: Mar. 11, 2010

(87) PCT Pub. No.: WO2009/012595
PCT Pub. Date: Jan. 29, 2009

(65) Prior Publication Data
US 2011/0053287 A1    Mar. 3, 2011

Related U.S. Application Data

(60) Provisional application No. 60/952,115, filed on Jul. 26, 2007.

(51) Int. Cl.
*G01N 33/92* (2006.01)
*G01N 24/00* (2006.01)
(52) U.S. Cl. .......................................... 436/71; 436/173
(58) Field of Classification Search .................. None
See application file for complete search history.

(56) References Cited

U.S. PATENT DOCUMENTS

| 7,348,143 B2 | 3/2008 | Heath et al. |
| 7,349,809 B2 | 3/2008 | Goodenowe |
| 2009/0057553 A1 | 3/2009 | Goodenowe |

FOREIGN PATENT DOCUMENTS

| WO | 0157518 A1 | 8/2001 |
| WO | 03/081506 A1 | 10/2003 |
| WO | 2007/030948 A1 | 3/2007 |

OTHER PUBLICATIONS

Duran in "The Laboratory Diagnosis of Peroxisomal Disease", Sep. 2007 http://www.erndim.unibas.ch/Meeting_Rep/07_sept_hamburg/R.%020Duran%20lab%20diagnosis.pdf.*
Bell "Phospholipid Spectrum Disorders in Autism", Aug. 11, 2010, http://www.medref.se/eyeq/bell.pdf.*
Vancassel et al. "Plasma fatty acid levels in autistic children", Prostaglandins, Leukotrienes and Essential Fatty Acids, 2001, v. 65, No. 1, pp. 1-7.*
Langford, "A Comprehensive Guide to Managing Autism", http://www.platovisit.nl/ntk/managing%20autism.pdf, 2002, edited in 2004.*

(Continued)

*Primary Examiner* — Yelena G Gakh
(74) *Attorney, Agent, or Firm* — LeClairRyan, a Professional Corporation

(57) ABSTRACT

Methods for the diagnosis, risk assessment, and monitoring of Autism Spectrum Disorder (ASD) are disclosed. More specifically the present invention relates to the measurement of small molecules (metabolites) in human plasma that are found to have different abundances between persons with a clinical manifestation of ASD and subjects not expressing symptoms of ASD. Further, this invention relates to the monitoring of putative therapeutic strategies designed to ameliorate the biochemical abnormalities associated with ASD.

18 Claims, 6 Drawing Sheets

| Autism vs. Control (No Carnitine) | | | | | | | | | | | |
|---|---|---|---|---|---|---|---|---|---|---|---|
| | C18 | C20 | C22 | C24 | C26 | C28 | C30 | C32 | C34 | C36 | C38 | C40 |
| 0db | ↑ | ↑ | ↑↑ | ↑ | ↑↑ | ↑↑ | ↑ | | ↑ | ↑ | ↑ | ↑ |
| 1db | ↓ | | ↑ | ↑ | ↑ | ↑ | ↑ | | | | | |
| 2db | | | | | | ↑ | ↑ | | | | | ↑ |
| 3db | ↓ | ↓ | ↓ | ↓ | | | | | | | | ↑ |
| 4db | ND | | | | | | | | | | | |
| 5db | ND | | | ↑ | | | | | | | | |
| 6db | ND | ↑↑ | ↑↑ | ↑↑ | ↑ | ↑ | | ↑ | | | | |

| Autism vs. Control (Carnitine) | | | | | | | | | | | |
|---|---|---|---|---|---|---|---|---|---|---|---|
| | C18 | C20 | C22 | C24 | C26 | C28 | C30 | C32 | C34 | C36 | C38 | C40 |
| 0db | | | | | | | ↑ | ↑ | ↑↑ | ↑ | ↑ | ↑ |
| 1db | ↑↑ | | | | | ↑ | | | ↑↑ | ↑ | | ↑ |
| 2db | ↑↑ | | | | | ↑ | ↑↑ | | ↑ | | ↑ | |
| 3db | | | | ↑ | ↑ | ↑ | ↑ | ↑ | ↑ | | | ↑↑ |
| 4db | ND | ↑↑ | ↑ | ↑ | ↑ | ↑ | ↑ | ↑ | ↑↑ | ↑↑ | ↑ | ↑ |
| 5db | ND | ↑ | ↑ | ↑ | ↑ | | ↑ | ↑ | ↑ | | | ↑ |
| 6db | ND | | | ↑ | ↑ | | ↑ | ↑ | ↑ | | | ↑ |

↑ <1.5, p<0.05
↑↑ >1.5, p<0.05
↓ <1.0, p<0.05
ND Not Determined db = double bond

OTHER PUBLICATIONS

Puri and Singh, "Normal phospholipid-related signal transduction in autism", Progress in Neuro-Psychopharmacology & Biological Psychiatry, 2002, v. 26, pp. 1405-1407.*

Wang et al. "Plasma Phospholipid Metabolic Profiling and Biomarkers of Type 2 Diabetes Mellitus Based on High-Performance Liquid Chromatography/Electrospray Mass Spectrometry and Multivariate Statistical Analysis", Anal. Chem. 2005, v. 77, pp. 4108-4116.*

Pulfer and Murphy, "Electrospray Mass Spectrometry of Phospholipids", Mass Spectrometry Reviews, 2003, v. 22, pp. 332-364.*

Heckenlively, "A Clear Biomarker for Autism?—The Question of Alterations in Lipid Metabolism", Jul. 2009 http://www.ageofautism.com/2009/07/a-clear-biomarker-for-autism-the-question-of-alterationsin-lipid-metabolism.html.*

Pastural et al. "Novel plasma phospholipid biomarkers of autism: Mitochondrial dysfunction as a putative causative mechanism", Prostaglandins, Leukotrienes and Essential Fatty Acids, 2009, v. 81. pp. 253-264.*

Bell et al. "Red Blood Cell Fatty Acid Compositions in a Patient With Autistic Spectrum Disorder: A Characteristic Abnormality in Neurodevelopmental Disorders," Prostaglandins, Leukotriens and Essential Fatty Acids 63(1/2):21-25 2000.

Bu et al. "Fatty Acid Compositions of Red Blood Cell Phospholipids in Children With Autism," Prostaglandins, Leukotriens and Essential Fatty Acids 74:215-221 2006.

Richardson et al. "Fatty Acid Metabolism in Neurodevelopmental Disorder: A New Perspective on Associations Between Attention-Deficit/Hyperactivity Disorder, Dyslexia, Dyspraxia and the Autism Spectrum," Prostaglandins, Leukotriens and Essential Fatty Acids 63(1/2):1-9 2000.

Sliwinski et al. "Polyunsaturated Fatty Acids: Do They Have a Role in the Pathophysiology of Autism?" Neuroendocrinology Letters 27(4):465-471 2006.

Bell et al. "Essential Fatty Acids and Phospholipase A2 in Autistic Spectrum Disorders," Prostaglandins, Leukotriens and Essential Fatty Acids 71:201-204 2004.

PCT International Search Report and Written Opinion for PCT/CA2008/001366, Jul. 25, 2008.

Zoroglu et al., "Increased Oxidative Stress and Altered Activities of Erythrocyte Free Radical Scavenging Enzymes in Autism," Eur. Arch. Psych. Clin. Neurosci. 254:143-147 (2004).

Taylor et al., "Is Autism a Disorder of Fatty Acid Metabolism? Possible Dysfunction of Mitochondrial Beta-Oxidation by Long Chain acyl-CoA Dehydrogenase," Med. Hypotheses 62:970-975 (2004).

James et al., "Metabolic Biomarkers of Increased Oxidative Stress and Impaired Methylation Capacity in Children with Autism," Am. J. Clin. Nutr. 80:1611-1617 (2004).

Kern et al., "Evidence of Toxicity, Oxidative Stress, and Neuronal Insult in Autism," J. Taxicol. Environ. Health (Part B) 9:485-499 (2006).

Lombard, "Autism: A Mitochondrial Disorder?" Med. Hypotheses 50:497-500 (1998).

Palmen et al., "Neuropathological Findings in Autism," Brain 127:2572-2583 (2004).

Pettegrew et al., "Acetyl-L-Carnitine Physical-Chemical, Metabolic, and Therapeutic Properties: Relevance for its Mode of Action in Alzheimer's Disease and Geriatric Depression," Mol. Psych. 5:616-632 (2000).

Sogut et al., "Changes in Nitric Oxide Levels and Antioxidant Enzyme Activities May Have a Role in the Pathophysiological Mechanisms Involved in Autism," Clin. Chim. Acta. 331:111-117 (2003).

Yorbik et al., "Investigation of Antioxidant Enzymes in Children with Autistic Disorder," Prostag. Leuko. Essential Fatty Acids 67(5):341-343 (2002).

* cited by examiner

Figure 1

| | C18 | C20 | C22 | C24 | C26 | C28 | C30 | C32 | C34 | C36 | C38 | C40 |
|---|---|---|---|---|---|---|---|---|---|---|---|---|
| Autism vs. Control (No Carnitine) | | | | | | | | | | | | |
| 0db | ← | ← | ←← | ← | ←← | ←← | ← |  | ← | ← | ← | ← |
| 1db | → |  | ← | ← |  | ← | ← |  |  |  |  |  |
| 2db |  |  |  |  |  | ← |  |  |  |  |  | ← |
| 3db | → |  | → | → |  |  |  |  |  |  |  | ← |
| 4db | ND |  |  | ← |  |  |  |  |  |  |  |  |
| 5db | ND |  |  |  |  |  |  |  | ← |  |  |  |
| 6db | ND | ←← | ←← | ←← | ← | ← |  |  |  |  |  |  |
| Autism vs. Control (Carnitine) | | | | | | | | | | | | |
| 0db |  |  |  |  |  | ← | ← | ← | ←← | ← | ← | ← |
| 1db |  | ←← |  |  | ← | ← | ← | ← | ← | ← | ← | ← |
| 2db |  | ←← |  | ← | ← | ←← | ←← | ← | ← |  |  |  |
| 3db |  |  |  | ← | ← |  | ← | ← |  |  | ← |  |
| 4db | ND |  | ← | ← | ← | ← |  |  | ←← | ←← |  | ←← |
| 5db | ND | ← | ← |  | ← |  |  |  | ← |  | ← | ← |
| 6db | ND |  |  |  |  |  |  |  |  | ← |  | ← |

← <1.5, p<0.05
←← >1.5, p<0.05
→ <1.0, p<0.05
ND Not Determined
db = double bond Levels of key DHA and AA containing PlsEtn and PtdEtn in longitudinal samples collected over the course of one year from individual subjects diagnosed with autism versus controls. Values are control-normalized and expressed as mean +/- SEM of the ratio to PtdEtn 16:0/18:0, n=3 for each child, n=30 for controls, *, p<0.05 vs. control.

Levels of key VLCFA containing PtdEtn in longitudinal samples collected over the course of one year from individual subjects diagnosed with autism versus controls. Values are control-normalized and expressed as mean +/- SEM of the ratio to PtdEtn 16:0/18:0, n=3 for each child, n=30 for controls, *, p<0.05 vs. control.

Levels of carnitine and O-acetylcarnitine in longitudinal samples collected over the course of one year from individual subjects diagnosed with autism versus controls. Values are control normalized and expressed as mean +/- SEM, n=3 for each child, n=30 for controls, *, p<0.05 vs. control.

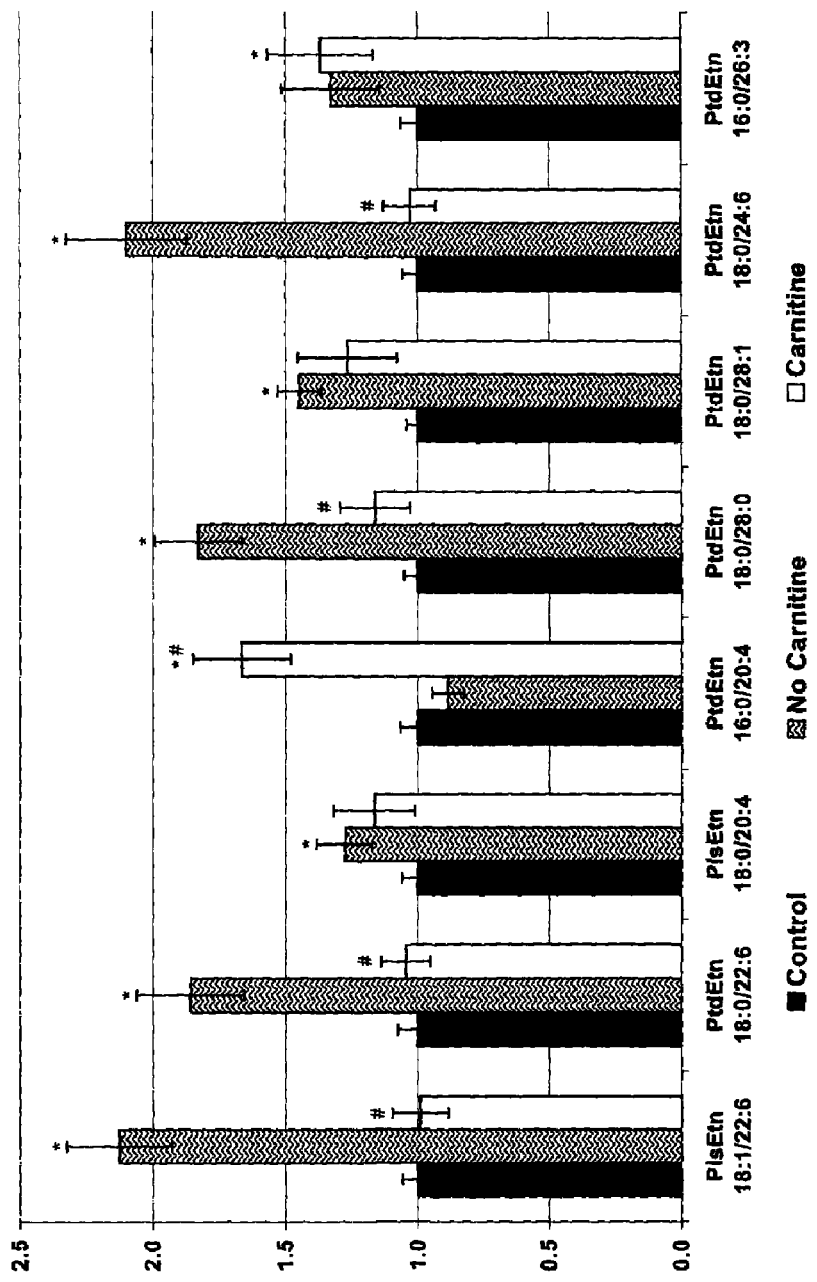

Figure 5

Levels of key DHA and AA containing PlsEtn and VLCFA containing PtdEtn in longitudinal samples collected over the course of one year from autistic subjects taking carnitine supplements [n=12 (4x3)] vs. subjects not taking carnitine supplements [n=33 (11x3)] and vs. controls [n=30 (10x3)]. Values control-normalized and expressed as mean +/- SEM of the ratio to PtdEtn 16:0/18:0. *, p<0.05 vs. control. #, p<0.05 vs. autism, no carnitine.

Within family comparison of key DHA containing PlsEtn and PtdEtn and AA containing PlsEtn in longitudinal samples collected over the course of one year from autistic subjects and their asymptomatic siblings. Values are control-normalized and expressed as mean +/- SEM of the ratio to PtdEtn 16:0/18:0, *, $p<0.05$ vs. control.

METHODS FOR THE DIAGNOSIS, RISK ASSESSMENT, AND MONITORING OF AUTISM SPECTRUM DISORDERS

This is a national stage application under 35 U.S.C. 371 of PCT/CA2008/001366, filed Jul. 25, 2008, which claims priority to U.S. Provisional Patent Application Ser. No. 60/952,115, filed Jul. 26, 2007.

FIELD OF THE INVENTION

The present invention relates to the diagnosis, risk assessment, and monitoring of Autism Spectrum Disorder (ASD). More specifically the present invention relates to the measurement of small molecules or metabolites that are found to have different abundances between persons with a clinical manifestation of ASD and subjects not expressing symptoms of ASD. Further, this invention relates to the monitoring of putative therapeutic strategies designed to ameliorate the biochemical abnormalities associated with ASD.

BACKGROUND

Autism is a lifelong disorder of unknown origin. The disorder is characterized by behavioural, developmental, neuropathological, and sensory abnormalities (American Psychiatric Association 1994) and is usually diagnosed between the ages of 3 and 10 with peak prevalence rates observed in children aged 5-8 (Yeargin-Allsopp, Rice et al. 2003). At this time, decreased cerebellar Purkinje cell density (Courchesne 1997; Palmen, van Engeland et al. 2004), increased oxidative stress (Yorbik, Sayal et al. 2002; Sogut, Zoroglu et al. 2003; Chauhan, Chauhan et al. 2004; James, Cutler et al. 2004; Zoroglu, Armutcu et al. 2004; Chauhan and Chauhan 2006), and abnormal methionine/homocysteine metabolism (James, Cutler et al. 2004) are the only robust biological characteristics of autism.

Although there is debate as to whether autism has a pre- (Courchesne, Redcay et al. 2004) or post-natal origin (Kern and Jones 2006), it is generally accepted that the symptoms and pathology persist throughout the life of the subject (Bauman and Kemper 2005). These findings suggest that there is an underlying and ongoing biochemical abnormality in autism, regardless of its origin. However, no such underlying biochemical abnormalities have been reported that correlate with the etiology or symptomology of ASD. As such, there is no biochemical test for autism.

Accordingly there is a need for methods that can diagnose ASD in subjects suspected of having ASD or methods that can identify subjects that are at risk of ASD and furthermore there is a need for methods that can assist in the monitoring of therapeutic strategies for the treatment of ASD.

SUMMARY

It has been determined that subjects with clinically diagnosed ASD have different abundances of small molecules or metabolites in their blood plasma relative to non-ASD subjects. It has further been determined that some high risk subjects (i.e. family history) with little or no ASD symptoms exhibit a biochemical phenotype analogous to that of subjects with a full clinical ASD phenotype. As such, methods for diagnosing ASD and for diagnosing elevated risk of ASD are provided.

It has been determined that subjects clinically diagnosed with ASD can be biochemically characterized as having a phenotype generally described by either:

a) elevated levels of saturated or monounsaturated very long chain fatty acid (VLCFA) containing phospholipids;

b) elevated levels of docosahexaenoic acid (22:6, DHA) containing phospholipids;

c) elevated levels of polyunsaturated VLCFA containing phospholipids; or d) combinations thereof.

It has further been determined that an experimental ASD therapeutic (Acetyl-Carnitine) can modify the above biochemical ASD phenotype such that some ASD biochemical markers return to non-ASD levels and that some ASD biochemical markers remain unchanged. It has further been determined that ASD subjects taking acetyl-carnitine exhibit biochemical changes that differentiate them from both ASD subjects not taking carnitine as well as non-ASD subjects not taking acetyl-carnitine. As such, methods for the monitoring of experimental ASD therapeutics in general and for the specific monitoring of acetyl-carnitine therapy are provided.

A method for the differential biochemical characterization of subjects presenting with ASD is provided. This differential biochemical characterizing has ramifications on the treatment and management of subjects presenting ASD symptoms. Firstly, it has been determined that ASD subjects with similar clinical phenotypes have dramatically different biochemical phenotypes. These findings indicate that different therapeutic strategies may need to be developed for different ASD subjects depending on the subject's biochemical phenotype. More importantly, the present findings indicate that the monitoring of the dose and therapeutic effectiveness of an ASD therapeutic in a subject diagnosed with ASD is preferably personalized to that particular subject's biochemical profile. For example, in subjects exhibiting high saturated VLCFA levels, the monitoring of saturated VLCFA levels may represent the most sensitive determiner of effective therapy or dosage, but such measurements may be of little or no value to an ASD subject exhibiting high polyunsaturated VLCFA levels and normal saturated VLCFA levels.

In one illustrative embodiment, the present invention provides for a method for diagnosing a human subject's health state or change in health state for Autism Spectrum Disorder (ASD) or identifying a human subject's risk of ASD, the method comprising the steps of:

a) analyzing a sample obtained from a patient to obtain quantifying data for one or more accurate masses;

b) comparing the quantifying data for said one or more accurate masses to corresponding data obtained from one or more reference samples; and c) using said comparison to diagnose the human subject's health state or change in health state for ASD based on the differences between the quantifying data and the corresponding data of the one or more accurate masses; wherein the one or more accurate masses is listed in any one of Tables 2 to 10.

In another illustrative embodiment, the present invention provides for a method for diagnosing a human subject's health state or change in health state for Autism Spectrum Disorder (ASD) or identifying a human subject's risk of ASD, the method comprising the steps of:

a) analyzing a sample obtained from a patient to obtain quantifying data for one or more of the following:
saturated or monounsaturated very long chain fatty acid (VLCFA) containing phospholipids;

docosahexaenoic acid (22:6, DHA) containing phospholipids;

DHA precursors (24:5, 24:6);

catabolic products of DHA beta-oxidation (20:6);

polyunsaturated VLCFA containing phospholipids; and combinations thereof;

b) comparing the quantifying data to corresponding data obtained from one or more reference samples; and c) using said comparison to diagnose the human subject's health state or change in health state for ASD based on having one of the following characterizations when compared to the corresponding data obtained from one or more reference samples:

elevated levels of saturated or monounsaturated very long chain fatty acid (VLCFA) containing phospholipids;

elevated levels of docosahexaenoic acid (22:6, DHA) containing phospholipids;

elevated levels of DHA precursors (24:5, 24:6);

elevated levels of catabolic products of DHA beta-oxidation (20:6);

elevated levels of polyunsaturated VLCFA containing phospholipids; or combinations thereof.

In another illustrative embodiment, the present invention provides for a method for diagnosing a human subject's health state or change in health state for Autism Spectrum Disorder (ASD) or identifying a human subject's risk of ASD, the method comprising the steps of:

a) analyzing a sample obtained from a patient to obtain quantifying data for one or more metabolites;

b) comparing the quantifying data for said one or more metabolites to corresponding data obtained from one or more reference samples; and c) using said comparison to diagnose the human subject's health state or change in health state for ASD based on the differences between the quantifying data and the corresponding data of the one or more metabolites wherein the one or more metabolites is listed in any one of Tables 3 to 10.

In another illustrative embodiment, the present invention provides for a method for diagnosing a human subject's health state or change in health state for Autism Spectrum Disorder (ASD) or identifying a human subject's risk of ASD, the method comprising: comparing quantifying data comprising one or more accurate masses listed in any one of Tables 2 to 10 of a sample from the human subject to corresponding data obtained from one or more reference samples; wherein the human subject's health state or change in health state for Autism Spectrum Disorder (ASD) or risk of ASD is based on a difference in intensity of the one or more accurate masses between the sample from the human subject and one or more reference samples.

In another illustrative embodiment, the present invention provides for a method for diagnosing a human subject's health state or change in health state for Autism Spectrum Disorder (ASD) or identifying a human subject's risk of ASD, the method comprising: comparing quantifying data comprising one or more metabolites listed in any one of Tables 3 to 10 of a sample from the human subject to corresponding data obtained from one or more reference samples; wherein the human subject's health state or change in health state for Autism Spectrum Disorder (ASD) or risk of ASD is based on a difference in intensity of the one or more metabolites between the sample from the human subject and one or more reference samples.

BRIEF DESCRIPTION OF THE DRAWINGS

These and other features of the invention will become more apparent from the following description in which reference is made to the appended drawings wherein:

FIG. 1 is a summary of PtdEtn (phosphatidlyethanolamine) changes in plasma of autistic subjects;

FIG. 5 is a graph illustrating levels of key DHA and AA containing PlsEtn and VLCFA containing PtdEtn in longitudinal samples collected over the course of one year from autistic subjects taking carnitine supplements [n=12 (4×3)] vs. subjects not taking carnitine supplements [n=33 (11×3)] and vs. controls [n=30 (10×3)]. Values control-normalized and expressed as mean+/−SEM of the ratio to PtdEtn 16:0/18:0, *, p<0.05 vs. control, #, p<0.05 vs. autism, no carnitine.

DETAILED DESCRIPTION

Figure 2:
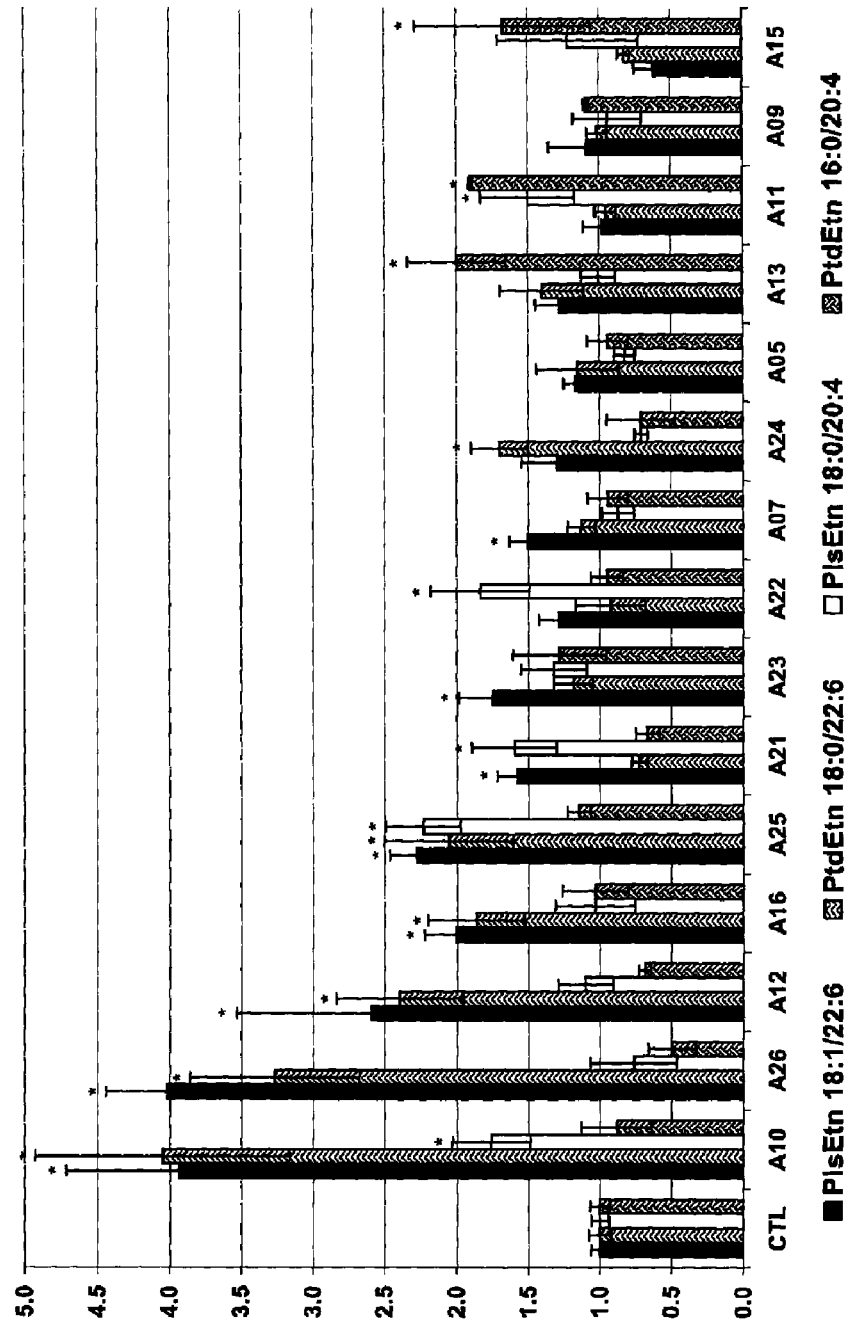
FIG. 2 is a graph illustrating levels of key DHA and arachidonic acid (AA) containing PlsEtn (plasmenylethanolamine) and PtdEtn in longitudinal samples collected over the course of one year from individual subjects diagnosed with autism versus controls. Values are control-normalized and expressed as mean+/−SEM of the ratio to PtdEtn 16:0/18:0, n=3 for each child, n=30 for controls, *, p<0.05 vs. control.

Small molecules or metabolites that are found to have different abundances between clinically diagnosed ASD, and normal patients expressing no symptoms of ASD have been identified. Based on these differences, a subject's health state or change in health state with respect to ASD may be determined. Methods for diagnosing a subject's health state, for example for diagnosing the presence or absence of ASD are provided, and methods for diagnosing a change in health state, for example for monitoring an ASD therapy, are provided.

Illustrative methods for diagnosing a subject's health state or change in health state with regard to ASD of the present invention comprise the steps of:

a) analyzing a sample(s) obtained from a human subject to obtain quantifying data for one or more than one metabolite marker or accurate mass;

b) comparing the quantifying data for said one or more than one metabolite marker or accurate mass to corresponding data obtained from one or more than one reference sample; and c) using said comparison to arrive at a determination of the subject's health state or change in health state.

The illustrative methods may further include the preliminary step of obtaining one or more than one sample from the human subject for analysis.

By the term "metabolite", it is meant specific small molecules, the levels or intensities of which are measured in a sample, and that may be used as markers to diagnose a disease state. These small molecules may also be referred to herein as "metabolite marker", "metabolite component", "biomarker", or "biochemical marker".

In one illustrative embodiment there is provided a method for diagnosing the biochemical ASD phenotype of a subject, comprising the steps of: introducing one or more than one sample from one or more than one patient with probable ASD into a high resolution mass spectrometer (for example, and without wishing to be limiting, a Fourier Transform Ion Cyclotron Resonance Mass Spectrometer (FTMS)); obtaining quantifying data for one or more than one metabolite marker; optionally creating a database of said quantifying data; comparing the quantifying data from the sample with corresponding reference data collected from non-ASD subjects; and using said comparison to determine the biochemical ASD phenotype of the subject. The biochemical ASD phenotype of the subject may be determined based on the differences identified when comparing the quantifying data from the sample with the corresponding reference data. The differences between ASD and non-ASD subjects are described in any one of Tables 2, 11-18.

In another illustrative embodiment there is provided a method for identifying subjects at risk of ASD, comprising the steps of: introducing one or more than one sample from one or more than one subject of unknown ASD status into a high resolution mass spectrometer (for example, and without wishing to be limiting, a Fourier Transform Ion Cyclotron Resonance Mass Spectrometer (FTMS)); obtaining quantifying data for one or more than one of the parent masses listed in any one of tables 2-10; optionally creating a database of said quantifying data; comparing the quantifying data from the sample with corresponding reference data collected from non-ASD subjects; and using said comparison to determine whether the subject has elevated risk of ASD.

In another illustrative embodiment there is provided a method for monitoring an ASD therapy, comprising the steps of: introducing a plurality of samples from one or more than one ASD subject into a high resolution mass spectrometer (for example, and without wishing to be limiting, a Fourier Transform Ion Cyclotron Resonance Mass Spectrometer (FTMS)); obtaining quantifying data for one or more than one of the parent masses listed in any one of tables 2-10; optionally creating a database of said quantifying data; comparing the quantifying data from the plurality of samples with each other and with corresponding reference data collected from non-ASD subjects and/or with previous collected quantifying data from a pre-therapy stage or an earlier-therapy stage of the subject(s) and using said comparison to determine whether the therapeutic strategy had a positive, negative, or no effect on the subject's underlying biochemical phenotype.

In another illustrative embodiment there is provided a method for diagnosing the biochemical ASD phenotype of a subject, comprising the steps of: introducing one or more than one sample from one or more than one patient with clinically diagnosed ASD into a multi-stage mass spectrometer (for example, and without wishing to be limiting, a triple quadrupole mass spectrometer (TQ)); obtaining quantifying data for one or more than one of the metabolites listed in any one of Tables 3-10; optionally creating a database of said quantifying data; comparing the quantifying data from the sample with corresponding reference data collected from non-ASD subjects; and using said comparison to determine whether the subject has ASD.

In another illustrative embodiment there is provided a method for identifying subjects at risk of ASD, comprising the steps of: introducing one or more than one sample from one or more than one subject of unknown ASD status into a multi-stage mass spectrometer (for example, and without wishing to be limiting, a triple quadrupole mass spectrometer (TQ)); obtaining quantifying data for one or more than one of the metabolites listed in any one of Tables 3-10; optionally creating a database of said quantifying data; comparing the quantifying data from the sample with corresponding reference data collected from non-ASD subjects; and using said comparison to determine whether the subject has elevated risk of ASD.

In another illustrative embodiment there is provided a method for monitoring an ASD therapy, comprising the steps of: introducing a plurality of samples from one or more than one ASD subject into a multi-stage mass spectrometer (for example, and without wishing to be limiting, a triple quadrupole mass spectrometer (TQ)); obtaining quantifying data for one or more than one of the metabolites listed in any one of Tables 3-10; optionally creating a database of said quantifying data; comparing the quantifying data from the plurality of samples with each other and/or with corresponding reference data collected from non-ASD subjects and/or with previously collected quantifying data from a pre-therapy stage or an earlier-therapy stage of the subject(s) and using said comparison to determine whether the therapeutic strategy had a positive, negative, or no effect on the subject's underlying biochemical phenotype.

In another illustrative embodiment there is provided a method for diagnosing the biochemical ASD phenotype of a subject, comprising the steps of: obtaining quantifying data for one or more than one of the metabolites listed in any one of Tables 2-10 from one or more than one ASD subject; optionally creating a database of said quantifying data; comparing the quantifying data from the sample with corresponding reference data collected from non-ASD subjects; and using said comparison to determine whether the subject has ASD.

In another illustrative embodiment there is provided a method for identifying subjects at risk of ASD, comprising the steps of: obtaining quantifying data for one or more than one of the metabolites listed in any one of Tables 2-10 from one or more than one subject of unknown ASD status; optionally creating a database of said quantifying data; comparing the quantifying data from the sample with corresponding reference data collected from non-ASD subjects; and using said comparison to determine whether the subject has elevated risk of ASD.

In another illustrative embodiment there is provided a method for monitoring an ASD therapy, comprising the steps of: obtaining quantifying data for one or more than one of the metabolites listed in any one of Tables 2-10 from a plurality of samples collected from one or more than one ASD subject; optionally creating a database of said quantifying data; comparing the quantifying data from the plurality of samples with each other and/or with corresponding reference data collected from non-ASD subjects and/or with previously collected quantifying data from a pre-therapy stage or an earlier-therapy stage of the subject(s); and using said comparison to determine whether the therapeutic strategy had a positive, negative, or no effect on the subject's underlying biochemical phenotype.

As would be obvious to anyone skilled in the art, other analytical technologies other than those illustrated above may be used to quantify the metabolites listed in Tables 2-10 including colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems.

As outlined above, illustrative methods for diagnosing a subject's health state or change in health state with regard to ASD of the present invention comprise the steps of:
a) analyzing a sample(s) obtained from a human subject to obtain quantifying data for one or more than one metabolite marker;
b) comparing the quantifying data for said one or more than one metabolite marker to corresponding data obtained from one or more than one reference sample; and
c) using said comparison to arrive at a determination of the subject's health state or change in health state.

The illustrative methods may further include the preliminary step of obtaining one or more than one sample from the human subject for analysis.

The step of analyzing the sample (step a) may comprise analyzing the sample using a mass spectrometer (MS). For example, and without wishing to be limiting, such mass spectrometer may be of the FTMS, orbitrap, time of flight (TOF), magnetic sector, linear ion trap (LIT) or quadrupole types. Alternatively, the mass spectrometer may be equipped with an additional pre-detector mass filter. For example, and without wishing to be limiting, such instruments are commonly referred to as quadrupole-FTMS (Q-FTMS), quadrupole-TOF (Q-TOF) or triple quadrupole (TQ or QQQ). In addition, the mass spectrometer may be operated in either the parent ion detection mode (MS) or in MSn mode, where $n>=2$. MSn refers to the situation where the parent ion is fragmented by collision induced dissociation (CID) or other fragmentation procedures to create fragment ions, and then one or more than one of said fragments are detected by the mass spectrometer. Such fragments may then be further fragmented to create further fragments. Alternatively, the sample may be introduced into the mass spectrometer using a liquid or gas chromatographic system or by direct injection.

By the term "differential diagnosis" or "differentially diagnosing", it is meant that various aspects of a disease state may be distinguished from one another. In particular, the methods disclosed herein allow for differential diagnosis of various biochemical phenotypes of ASD; for example and without wishing to be limiting, the methods disclosed herein may provide the diagnosis of subjects with or at risk of ASD with the biochemical phenotype of:
a) elevated levels of saturated or monounsaturated very long chain fatty acid (VLCFA) containing phospholipids;
b) elevated levels of docosahexaenoic acid (22:6, DHA) containing phospholipids;
c) elevated levels of polyunsaturated VLCFA containing phospholipids; or
d) combinations thereof, In accordance with the methods disclosed herein, any type of biological sample that originates from anywhere within the body, for example but not limited to, blood (serum/plasma), CSF, urine, stool, breath, saliva, or biopsy of any solid tissue including tumor, adjacent normal, smooth and skeletal muscle, adipose tissue, liver, skin, hair, brain, kidney, pancreas, lung, colon, stomach, or other may be used. Of particular interest are samples that are plasma. While the term "plasma" is used herein, those skilled in the art will recognize that serum or whole blood or a sub-fraction of whole blood may also be used. CSF may be obtained by a lumbar puncture requiring a local anesthetic.

In a non-limiting example, when a blood sample is drawn from a patient there are several ways in which the sample may be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are within the scope of the methods described herein.

Without wishing to be limiting, the processed blood or plasma sample described above may then be further processed to make it compatible with the methodical analysis technique to be employed in the detection and measurement of the metabolites contained within the processed blood sample. The types of processing can range from as little as no further processing to as complex as differential extraction and chemical derivatization. Extraction methods may include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. A method of particular interest for extracting metabolites for FTMS non-targeted analysis and for flow injection LC-MS/MS analysis is to perform a liquid/liquid extraction whereby non-polar metabolites dissolve in an organic solvent and polar metabolites dissolve in an aqueous solvent.

The extracted samples may be analyzed using any suitable method including those known in the art. For example, and without wishing to be limiting, extracts of biological samples are amenable to analysis on essentially any mass spectrometry platform, either by direct injection or following chromatographic separation. Typical mass spectrometers are comprised of a source that ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof. The advantage of FTMS over other MS-based platforms is its high resolving capability that allows for the separation of metabolites differing by only hundredths of a Dalton, many of which would be missed by lower resolution instruments.

The metabolites are generally characterized by their accurate mass, as measured by mass spectrometry technique. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm difference in the accurate mass would indicate the same metabolite. The accurate mass is given as the mass of the neutral metabolite. During the ionization of the metabolites, which occurs during analysis of the sample, the metabolite will cause either a loss or gain of one or more hydrogen atoms and a loss or gain of an electron. This changes the accurate mass to the "ionized mass", which differs from the accurate mass by the mass of hydrogen atoms and electrons lost or gained during ionization. Unless otherwise specified, the accurate neutral mass will be referred to herein.

Similarly, when a metabolite is described by its molecular formula, the molecular formula of the neutral metabolite will be given. Naturally, the molecular formula of the ionized metabolite will differ from the neutral molecular formula by the number of hydrogen atoms lost or gained during ionization or due to the addition of a non-hydrogen adduct ion.

Data is collected during analysis and quantifying data for one or more than one metabolite is obtained. "Quantifying data" is obtained by measuring the levels or intensities of specific metabolites present in a sample.

The quantifying data is compared to corresponding data from one or more than one reference sample. The "reference sample" is any suitable reference sample for the particular disease state. For example, and without wishing to be limiting in any manner, the reference sample may be a sample from a control individual, i.e., a person not suffering from ASD with or without a family history of ASD (also referred to herein as a "'normal' counterpart"); the reference sample may also be a sample obtained from a patient clinically diagnosed with ASD. As would be understood by a person of skill in the art, more than one reference sample may be used for comparison to the quantifying data. For example and without wishing to be limiting, the one or more than one reference sample may be a first reference sample obtained from a non-ASD control individual. The one or more than one reference sample may further include a second reference sample obtained from a patient with clinically diagnosed ASD of the peroxisomal type, a third reference sample obtained from a patient with clinically diagnosed ASD of the mitochondrial type, a fourth reference sample obtained from a patient suffering from clinically diagnosed ASD of an unknown type, or any combination thereof. In the case of monitoring a subjects change in disease state, the reference sample may include a sample obtained an earlier time period either pre-therapy or during therapy to compare the change in disease state as a result of therapy.

Methods within the scope of the present invention will be further illustrated in the following non-limiting examples.

EXAMPLE 1

Identification of ASD Subjects Using Accurate Mass Biomarkers

Sample Collection. Three plasma samples were collected from 15 clinically diagnosed ASD subjects and 12 non-ASD controls over a 12 month period (six month interval between samplings).

Sample extraction. Plasma samples were stored at −80° C. until thawed for analysis. All extractions were performed on ice. Metabolites were extracted using 1% ammonium hydroxide and ethyl acetate (EtOAc) in the ratio of 1:1:5, respectively, three times followed by two more extractions with 0.33% formic acid and EtOAc in the ratio of 1:1:5. Samples were centrifuged between extractions at 4° C. for 10 min at 3500 rpm, and the organic layers combined. The organic and aqueous extracts were then stored at −80° C. until analysis.

Mass Spectrometric Analysis. Plasma extracts were analyzed by direct injection into a FTMS and ionization by either ESI or atmospheric pressure chemical ionization (APCI) in both positive and negative modes. Sample extracts were diluted either three or six-fold in methanol:0.1% (v/v) ammonium hydroxide (50:50, v/v) for negative ionization modes, or in methanol:0.1% (v/v) formic acid (50:50, v/v) for positive ionization modes. For APCI, sample extracts were directly injected without diluting. All analyses were performed on a Bruker Daltonics APEX III Fourier transform ion cyclotron resonance mass spectrometer equipped with a 7.0 T actively shielded superconducting magnet (Bruker Daltonics, Billerica, Mass.). Samples were directly injected using electrospray ionization (ESI) and/or APCI at a flow rate of 1200 µL per hour. Ion transfer/detection parameters were optimized using a standard mix of serine, tetra-alanine, reserpine, Hewlett-Packard tuning mix and the adrenocorticotrophic hormone fragment 4-10. In addition, the instrument conditions were tuned to optimize ion intensity and broad-band accumulation over the mass range of 100-1000 amu according to the instrument manufacturer's recommendations. A mixture of the above mentioned standards was used to internally calibrate each sample spectrum for mass accuracy over the acquisition range of 100-1000 amu.

In total, six separate analyses comprising combinations of extracts and ionization modes were obtained for each sample:
Aqueous Extract
1. Positive ESI (analysis mode 1101)
2. Negative ESI (analysis mode 1102)
Organic Extract
3. Positive ESI (analysis mode 1201)
4. Negative ESI (analysis mode 1202)
5. Positive APCI (analysis mode 1203)
6. Negative APCI (analysis mode 1204)

Mass Spectrometry Data Processing. Using a linear least-squares regression line, mass axis values were calibrated such that each internal standard mass peak had a mass error of <1 p.p.m. compared with its theoretical mass. Using XMASS software from Bruker Daltonics Inc., data file sizes of 1 megaword were acquired and zero-filled to 2 megawords. A sinm data transformation was performed prior to Fourier transform and magnitude calculations. The mass spectra from each analysis were integrated, creating a peak list that contained the accurate mass and absolute intensity of each peak. Compounds in the range of 100-2000 m/z were analyzed. In order to compare and summarize data across different ionization modes and polarities, all detected mass peaks were converted to their corresponding neutral masses assuming hydrogen adduct formation. A self-generated two-dimensional (mass vs. sample intensity) array was then created using DISCOVAmetrics™ software (Phenomenome Discoveries Inc., Saskatoon, SK, Canada). The data from multiple files were integrated and this combined file was then processed to determine the unique masses. The average of each unique mass was determined, representing the y-axis. This value represents the average of all of the detected accurate masses that were statistically determined to be equivalent. Considering that the mass accuracy of the instrument for the calibration standards is approximately 1 ppm, a person skilled in the art will recognize that these average masses may include individual masses that fall within +/−5 ppm of this average mass. A column was created for each file that was originally selected to be analyzed, representing the x-axis. The intensity for each mass found in each of the files selected was then filled into its representative x,y coordinate. Coordinates that did not contain an intensity value were left blank. Once in the array, the data were further processed, visualized and interpreted, and putative chemical identities were assigned. Each of the spectra were then peak picked to obtain the mass and intensity of all metabolites detected. These data from all of the modes were then merged to create one data file per sample. The data from all samples was then merged and aligned to create a two-dimensional metabolite array in which each sample was represented by a column and each unique metabolite was represented by a single row. In the cell corresponding to a given metabolite sample combination, the intensity of the metabolite in that sample was displayed. When the data is represented in this format, metabolites showing differences between groups of samples can be determined. Using this method, accurate mass features that differed between ASD subjects not taking carnitine supplements and non-ASD subjects. By using all or a subset of accurate masses described in Table 2, the methods disclosed herein allow for the diagnosis of ASD.

EXAMPLE 2

The Diagnosis and Individual Characterization of ASD Subjects Using LC-MS/MS and the Evaluation of a ASD Therapeutic Sample Collection. Three plasma samples were collected from 15 clinically diagnosed ASD subjects and 12 non-ASD controls over a 12 month period (six month interval between samplings). Four subjects were treated with carnitine (A09, A11, A13, A15). Table 1 outlines the clinical characteristics of the subjects studied. Social cognition scores were determined using methods known in the art. Although 12 non-autistic control subjects were enrolled, two siblings (C08 and C29) excluded from the control population for overall comparisons due to the fact that their plasma levels of PlsEtn 18:1/22:6 were significantly higher than the rest of the controls (p=5.6e-6 and 4.0e-4, respectively, FIG. 6).
Sample Extraction Was as Described in Example 1.

LC-MS/MS flow injection analyses. Analyses were performed using a linear ion trap mass spectrometer (4000 Q TRAP, Applied Biosystems) coupled with an Agilent 1100 LC system. Sample was prepared by adding 15 μL of internal standard (5 μg/mL of (24-$^{13}$C)-Cholic Acid (Cambridge Isotope Laboratories, Andover, Mass.) in methanol) to 120 μL ethyl acetate fraction of each sample. 100 μl of sample was injected by flow injection analysis (FIA), and monitored under negative APCI mode. The method was based on multiple reaction monitoring (MRM) of one parent/fragment transition for each metabolite and (24-$^{13}$C)-Cholic Acid. Each transition was scanned for 70 ms. 10% EtOAc in MeOH at a flow rate of 360 μl/min was used as the mobile phase. The source parameters were set as follows: CUR: 10.0, CAD: 8, NC: −4.0, TEM: 400, GS1: 30, GS2: 50, interface heater on. The compound parameters were set as follows: DP: −120.0, EP: −10, NC: −4.0, CE: −40, CXP: −15. Tables 3-10 lists the metabolites and the MS/MS transition that was used for each metabolite. A standard curve was generated for all analytes to verify instrument linearity by serial dilution of a healthy normal serum extract with constant concentration of (24-$^{13}$C)-Cholic Acid. All samples were analyzed in a randomized blinded manner and were bracketed by known serum standard dilutions. All standard curves had $r^2$ values >0.98.
Plasma PtdEtn, PlsEtn, and Autism In total, plasma levels of 136 PtdEtn and 15 PlsEtn species were measured. The results of these analyses are summarized in Tables 11-18 and in FIG. 1. The key observations for autistic subjects not taking carnitine were:
1. Levels of virtually all saturated VLCFA (SVLCFA) were significantly elevated;
2. Levels of 18:1 were decreased but levels of monounsaturated VLCFA (MUVLCFA) were elevated;
3. Levels of LCFA and VLCFA containing three double bonds were significantly decreased;
4. Levels of DHA (22:6), DHA precursors (24:5, 24:6), and catabolic products of DHA beta-oxidation (20:6) were all elevated;
5. Levels of PlsEtn containing DHA were elevated.

Plasma levels of 26:0 containing PtdEtn were not observed to be increased relative to 22:0 containing PtdEtn. These results are contrary to those observed from subjects suffering from peroxisomal disorders, where 26:0 is elevated to a much greater extent than 22:0 (Moser and Moser 1996). Therefore the methods described in this application provide a means to differentiate ASD from peroxisomal disorders.

Figure 3:
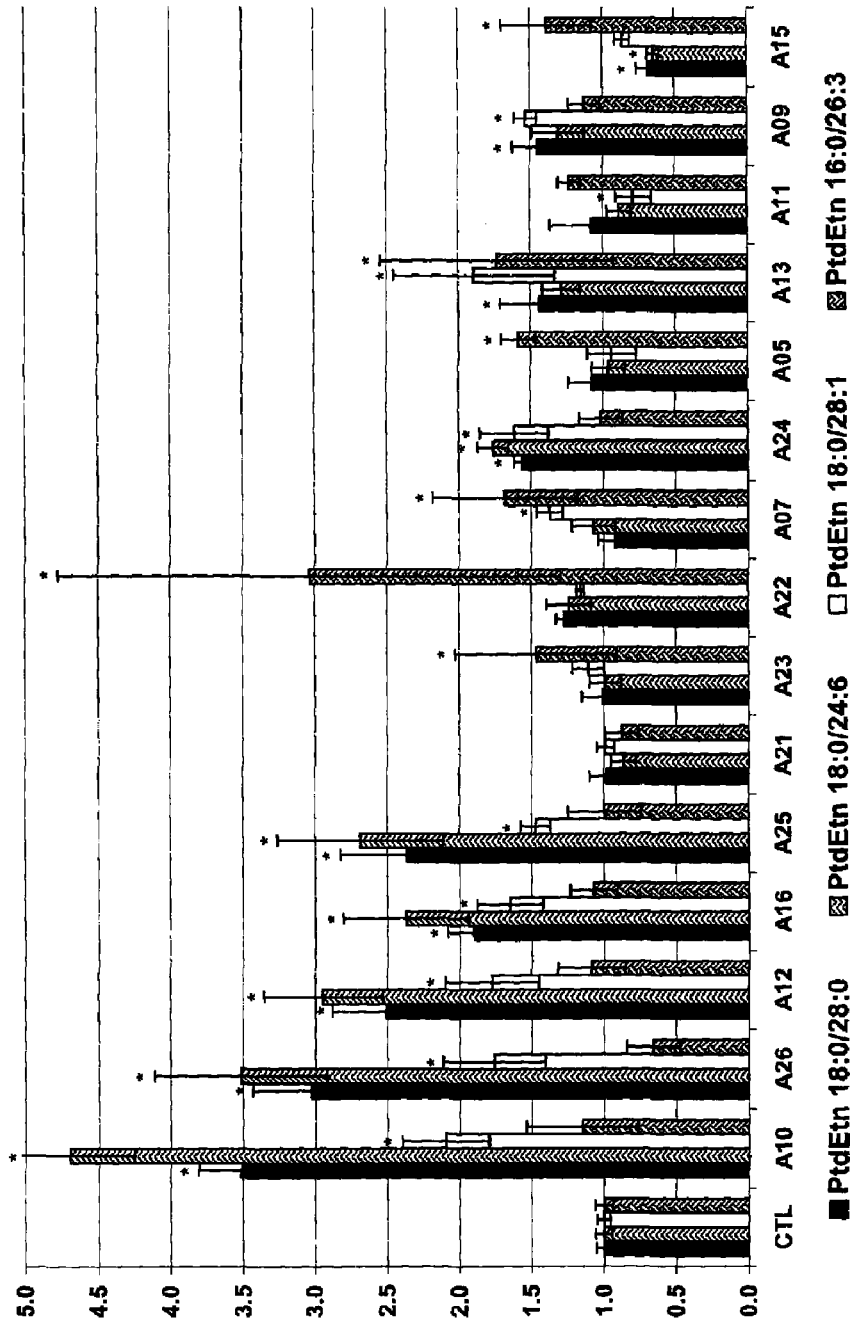
FIG. 3 is a graph illustrating levels of key VLCFA containing PtdEtn in longitudinal samples collected over the course of one year from individual subjects diagnosed with autism versus controls. Values are control-normalized and expressed as mean+/−SEM of the ratio to PtdEtn 16:0/18:0, n=3 for each child, n=30 for controls, *, p<0.05 vs. control.
Figure 6:
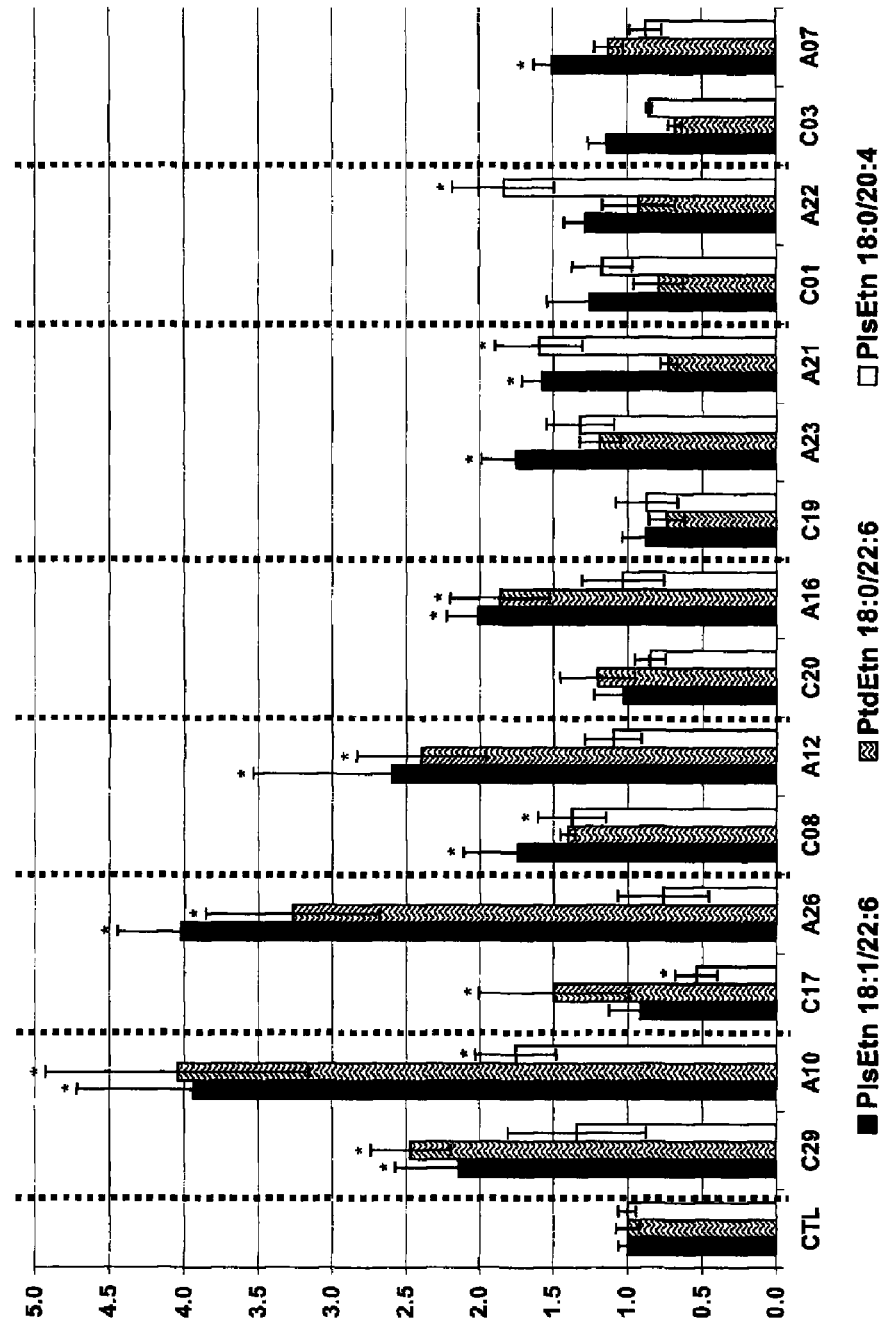
FIG. 6 is a graph illustrating a within family comparison of key DHA containing PlsEtn and PtdEtn and AA containing PlsEtn in longitudinal samples collected over the course of one year from autistic subjects and their asymptomatic siblings. Values are control-normalized and expressed as mean+/−SEM of the ratio to PtdEtn 16:0/18:0, *, p<0.05 vs. control.

These results indicate that all children with ASD exhibit a universal metabolic phenotype. The uncontrolled nature of the collection protocol was such that these findings represent a true sub-sampling of ASD subjects. Each subject was sampled at three different times over the course of one year and no dietary restrictions were imposed. Under these settings, 11/11 untreated ASD children exhibited the same biochemical phenotype, that is, statistically elevated levels of VLCFA and/or DHA containing phospholipids (FIGS. 2-3). In addition, in 8/8 families in which a non-ASD sibling was available for comparative analysis the ASD child had a more pronounced biochemical phenotype than the non-ASD sibling (FIG. 6). These metabolic abnormalities best fit a model of impaired mitochondrial fatty acid beta oxidation resulting in excessive extra-mitochondrial processing of palmitate.

EXAMPLE 3

Individual Subject Analyses

Since longitudinal samples were collected on all participants, it was possible to evaluate each participant separately. This analysis revealed dramatic subject-to-subject variability but relatively modest within subject variability, considering that the three samples were collected over the course of an entire year. As described above, all ASD subjects exhibit the same underlying metabolic abnormality—the excessive extramitochondrial processing of palmitate. However, the actual biochemical manifestation and diagnosis of this abnormality was observed to have various subject-to-subject variability. To illustrate this phenomenon, Tables 2 and 3 display the individual profiles of eight prototypical biomarkers representative of the 5 metabolite changes described in Example 2 (note that the last 4 subjects were taking acetyl-carnitine and are not part of this discussion). Table 2 focuses on DHA and AA containing PlsEtn and PtdEtn. As can be observed, only subjects A22 and A05 did not show a significantly elevated level of DHA containing PlsEtn or PtdEtn. However by looking at FIG. 3 it is observed that these 2 subjects have elevated levels of polyunsaturated VLCFA 26:3.

All of the autistic children not taking carnitine supplementation (11/11) were observed to have significantly higher levels (p<0.05) of either DHA-PlsEtn or VLCFA-PtdEtn (FIGS. 2 and 3).

EXAMPLE 4

Monitoring the Biochemical Efficacy of an Experimental ASD Therapy

Figure 4:
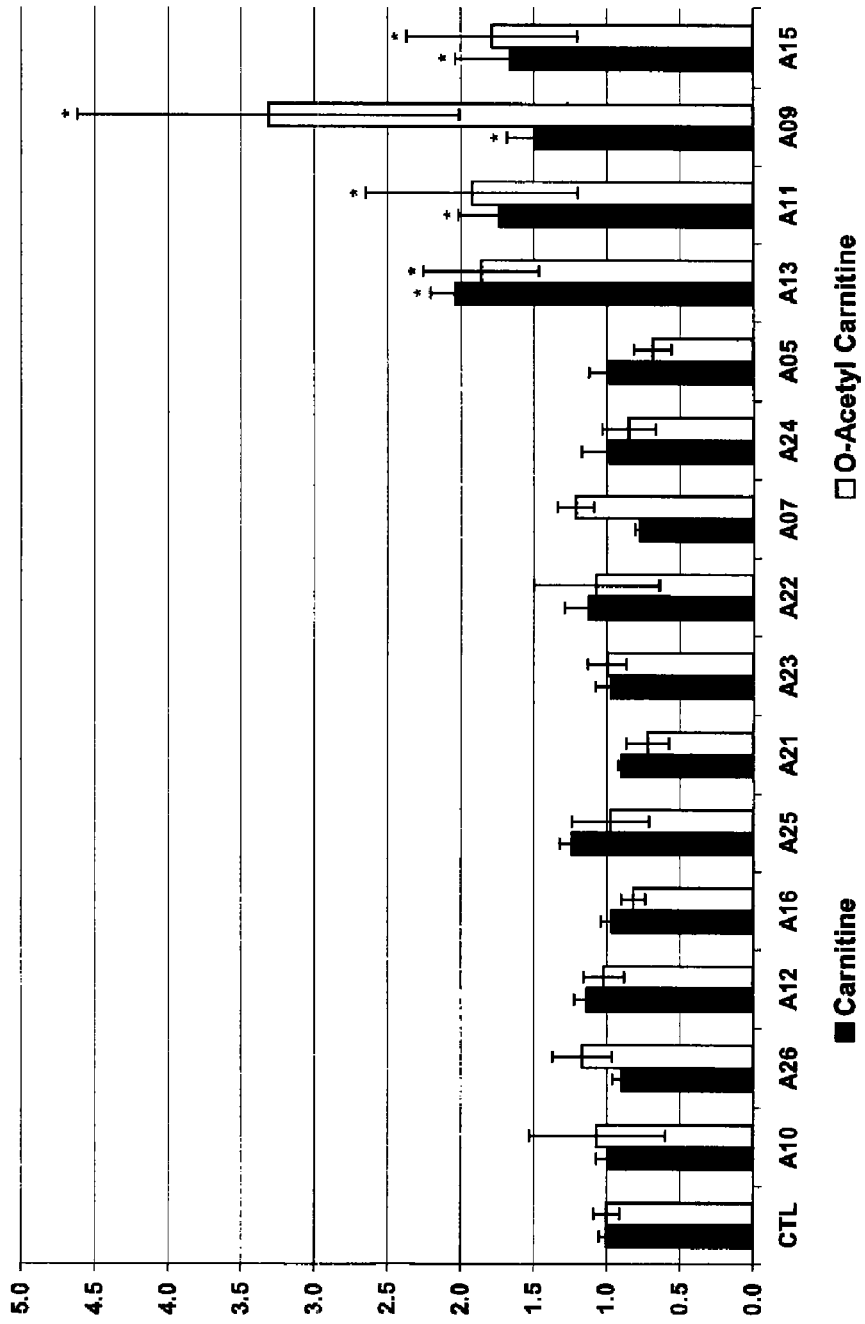
FIG. 4 is a graph illustrating levels of carnitine and O-acetylcarnitine in longitudinal samples collected over the course of one year from individual subjects diagnosed with autism versus controls. Values are control normalized and expressed as mean+/−SEM, n=3 for each child, n=30 for controls, *, p<0.05 vs. control.

It has been suggested that mitochondrial defects are associated with ASD (Lombard 1998; Clark-Taylor and Clark-Taylor 2004). Since acetyl-carnitine is known to have mitochondrial enhancing qualities (Pettegrew, Levine et al. 2000) it has been suggested as a possible therapeutic for ASD. Acetyl-carnitine is not approved nor has it been proven to be effective in ASD. To illustrate the utility of a method of monitoring ASD therapy as disclosed herein, the diagnostic ASD biomarkers described above were quantified in subjects taking acetyl-carnitine supplements. FIG. 4 illustrates the carnitine and acetyl carnitine levels in all of the subjects. None of the ASD subjects not taking carnitine exhibited either a deficiency or an elevation in either carnitine or acetyl-carnitine. All of the subjects taking acetyl-carnitine had elevated levels of both carnitine and acetyl-carnitine.

Comparison of the plasma levels of the eight most descriptive metabolites between the carnitine+/−autistic subjects and controls, determined that the effect of carnitine on the autism biomarkers was striking (FIG. 5). Complete normalization of DHA-PlsEtn, DHA-PtdEtn, the DHA precursor (24:6) and saturated VLCFA (28:0) was observed. Carnitine supplementation had no significant effect on 28:1 and 26:3 PdtEtn, suggesting that carnitine is only effective at modulating palmitate-derived elongation products. However, subjects taking carnitine had significantly elevated levels of AA-PtdEtn (20:4). These data suggest that carnitine is effective in preventing VLCFA, DHA, and DHA-PlsEtn accumulation by restoring palmitate oxidation in the mitochondria. However, the rate of elongation and desaturation of mono- and di-unsaturated fatty acid precursors appear to be unaffected and a compensatory elevation in AA appears to occur.

EXAMPLE 5

Identifying Subjects with Elevated Risk of ASD

For eight of the autistic children enrolled (excluding those taking carnitine), asymptomatic or mildly symptomatic siblings were followed simultaneously (Table 1). These subjects are considered high risk due to the increased prevalence of ASD in siblings (Newschaffer, Fallin et al. 2002). When the PlsEtn metabolites of FIG. 2 were plotted by family (FIG. 6), invariably, the affected sibling had higher levels of one of these metabolites than the non-affected sibling. This difference was statistically significant ($p<0.05$) in 5 of the 8 subjects. In two of the three situations in which the affected sibling was not observed to have significantly higher levels versus the non-affected sibling, the non-affected sibling had significantly elevated levels relative to controls. These subjects would be biochemically diagnosed as at risk of ASD. When these two control children (C29 and C08) were more closely evaluated for ASD symptoms using the social cognition test (Skuse 2000), it was observed that the male subject (C29) showed a social cognition deficit, whereas the female (C08) was completely asymptomatic (Table 1). The lack of effect in the female subject is not unexpected as females are thought to have a social cognition reserve. Based upon these findings the methods described in this application can effectively identify subjects at risk of ASD.

TABLE 1

Clinical information summary.

| | Sex | Age | Family History | Social Cognition |
|---|---|---|---|---|
| Controls Subject ID | | | | |
| F1, C29 | M | 5 | Y (A10) | 11 |
| F2, C08 | F | 7 | Y (A12) | 0 |
| F3, C20 | F | 17 | Y (A16) | 3 |
| F4, C17 | M | 9 | Y (A26) | 6 |
| F5, C19 | M | 6 | Y (A23, A21) | |
| F6, C03 | M | 7 | Y (A07) | 2 |
| F7, C02 | M | 15 | Y (A11, A15) | 1 |
| F7, C28 | M | 7 | Y (A11, A15) | 6 |
| F8, C01 | F | 4 | Y (A22) | |
| C, C04 | M | 11 | N | 0 |
| C, C14 | M | 8 | N | 2 |
| C, C27 | M | 8 | N | 4 |
| Autistic Subject ID | | | | |
| F1, A10 | M | 7 | | 18 |
| F2, A12 | M | 9 | | 16 |
| F3, A16 | M | 10 | | 23 |
| F4, A26 | M | 5 | | 9 |
| F5, A23 | M | 5 | Y (A21) | |
| F5, A21 | M | 8 | Y (A23) | 21 |
| F6, A07 | M | 10 | | 18 |
| F7, A11 (Carnitine) | M | 13 | Y (A15) | 23 |
| F7, A15 (Carnitine) | M | 8 | Y (A11) | 23 |
| F8, A22 | M | 6 | | |
| A, A05 | M | 13 | | |
| A, A24 | M | 7 | | 16 |
| A, A25 | M | 8 | | 16 |
| A, A09 (Carnitine) | M | 2 | Y (A13) | 14 |
| A, A13 (Carnitine) | M | 8 | Y (A09) | 19 |

TABLE 2

Accurate mass features differing between autistic subjects versus controls.

| Parent Mass | Analysis Mode | Control Average | SEM | Autism Average | SEM | Ratio | ttest |
|---|---|---|---|---|---|---|---|
| 820.5267 | 1204 | 3.03 | 0.14 | 6.07 | 0.58 | 2.01 | 6.9E−06 |
| 834.5398 | 1204 | 3.11 | 0.18 | 5.68 | 0.47 | 1.83 | 1.8E−05 |
| 328.2402 | 1202 | 6.52 | 0.52 | 16.31 | 2.31 | 2.50 | 6.0E−05 |
| 879.5992 | 1102 | 4.25 | 0.22 | 8.40 | 0.96 | 1.98 | 6.0E−05 |
| 806.5089 | 1204 | 6.43 | 0.43 | 11.97 | 1.28 | 1.86 | 9.7E−05 |
| 851.5694 | 1102 | 8.65 | 0.63 | 18.31 | 2.34 | 2.12 | 1.1E−04 |
| 807.5133 | 1204 | 4.10 | 0.28 | 7.52 | 0.79 | 1.83 | 1.3E−04 |
| 858.6834 | 1202 | 6.98 | 0.31 | 9.20 | 0.45 | 1.32 | 1.4E−04 |
| 792.4940 | 1204 | 5.24 | 0.29 | 9.54 | 1.05 | 1.82 | 1.6E−04 |
| 852.5719 | 1102 | 4.58 | 0.29 | 9.13 | 1.16 | 1.99 | 1.9E−04 |
| 878.7575 | 1204 | 7.87 | 0.64 | 4.71 | 0.46 | 0.60 | 3.3E−04 |
| 613.3380 | 1202 | 3.14 | 0.23 | 6.65 | 0.90 | 2.12 | 4.0E−04 |
| 622.4949 | 1203 | 3.36 | 0.18 | 5.46 | 0.52 | 1.63 | 4.1E−04 |
| 747.5203 | 1202 | 2.56 | 0.12 | 4.54 | 0.53 | 1.78 | 6.7E−04 |
| 837.5888 | 1202 | 4.48 | 0.18 | 6.18 | 0.46 | 1.38 | 7.3E−04 |
| 851.5681 | 1202 | 7.31 | 0.70 | 14.50 | 1.98 | 1.98 | 7.6E−04 |
| 858.6842 | 1102 | 14.36 | 0.59 | 18.20 | 0.99 | 1.27 | 1.2E−03 |
| 596.5017 | 1204 | 6.66 | 0.62 | 10.30 | 0.91 | 1.55 | 1.4E−03 |
| 852.5713 | 1202 | 4.10 | 0.35 | 7.40 | 0.97 | 1.80 | 1.5E−03 |
| 841.5387 | 1102 | 2.62 | 0.14 | 4.49 | 0.55 | 1.71 | 2.6E−03 |
| 550.4964 | 1203 | 40.21 | 4.56 | 23.19 | 2.97 | 0.58 | 3.2E−03 |
| 819.5794 | 1204 | 2.97 | 0.21 | 5.07 | 0.52 | 1.70 | 3.6E−03 |
| 859.6879 | 1102 | 7.29 | 0.30 | 8.96 | 0.47 | 1.23 | 3.7E−03 |
| 551.4998 | 1203 | 15.62 | 1.78 | 9.08 | 1.16 | 0.58 | 3.7E−03 |
| 828.5476 | 1201 | 7.13 | 0.46 | 11.30 | 1.37 | 1.59 | 3.8E−03 |
| 893.7762 | 1204 | 17.14 | 1.38 | 11.80 | 1.06 | 0.69 | 4.0E−03 |
| 750.5406 | 1204 | 4.76 | 0.44 | 7.83 | 0.98 | 1.64 | 4.8E−03 |
| 793.4944 | 1204 | 3.60 | 0.27 | 5.96 | 0.64 | 1.66 | 5.3E−03 |
| 791.5471 | 1204 | 6.06 | 0.69 | 11.08 | 1.59 | 1.83 | 5.4E−03 |
| 827.5440 | 1201 | 13.69 | 0.87 | 21.48 | 2.71 | 1.57 | 6.0E−03 |
| 879.5982 | 1202 | 3.25 | 0.26 | 5.12 | 0.58 | 1.57 | 6.4E−03 |
| 904.7514 | 1203 | 7.48 | 0.47 | 9.88 | 0.72 | 1.32 | 6.6E−03 |
| 906.7790 | 1204 | 10.73 | 0.81 | 7.85 | 0.64 | 0.73 | 7.7E−03 |

TABLE 2-continued

Accurate mass features differing between autistic subjects versus controls.

| Parent Mass | Analysis Mode | Control Average | SEM | Autism Average | SEM | Ratio | ttest |
|---|---|---|---|---|---|---|---|
| 905.7564 | 1203 | 4.94 | 0.24 | 6.28 | 0.43 | 1.27 | 7.9E−03 |
| 865.7508 | 1204 | 12.49 | 1.14 | 7.96 | 1.14 | 0.64 | 8.4E−03 |
| 753.5273 | 1201 | 3.95 | 0.28 | 2.99 | 0.19 | 0.76 | 8.5E−03 |
| 594.4849 | 1204 | 5.68 | 0.47 | 8.14 | 0.82 | 1.43 | 9.8E−03 |
| 218.2034 | 1203 | 2.97 | 0.11 | 3.43 | 0.13 | 1.16 | 9.8E−03 |
| 894.7838 | 1204 | 7.10 | 0.68 | 4.83 | 0.42 | 0.68 | 1.1E−02 |
| 558.4652 | 1204 | 2.46 | 0.15 | 3.28 | 0.26 | 1.34 | 1.2E−02 |
| 779.4864 | 1204 | 2.87 | 0.26 | 4.55 | 0.50 | 1.58 | 1.4E−02 |
| 595.4887 | 1204 | 2.86 | 0.24 | 3.94 | 0.33 | 1.38 | 1.4E−02 |
| 246.2345 | 1203 | 2.82 | 0.09 | 3.23 | 0.14 | 1.14 | 1.5E−02 |
| 596.5018 | 1202 | 5.30 | 0.55 | 7.62 | 0.74 | 1.44 | 1.5E−02 |
| 724.5244 | 1204 | 4.03 | 0.31 | 5.66 | 0.60 | 1.40 | 1.6E−02 |
| 775.5516 | 1204 | 5.24 | 0.48 | 8.69 | 1.21 | 1.66 | 1.7E−02 |
| 549.4840 | 1203 | 15.46 | 1.39 | 10.90 | 1.23 | 0.71 | 1.8E−02 |
| 866.7550 | 1204 | 7.92 | 0.67 | 5.48 | 0.71 | 0.69 | 1.9E−02 |
| 548.4807 | 1203 | 41.47 | 3.64 | 30.01 | 3.13 | 0.72 | 2.1E−02 |
| 258.2346 | 1203 | 3.56 | 0.13 | 3.99 | 0.13 | 1.12 | 2.3E−02 |
| 766.4787 | 1204 | 2.51 | 0.18 | 7.25 | 1.31 | 2.89 | 2.3E−02 |
| 329.2436 | 1202 | 2.74 | 0.18 | 5.09 | 0.65 | 1.86 | 2.3E−02 |
| 256.2189 | 1203 | 4.45 | 0.15 | 5.05 | 0.21 | 1.13 | 2.4E−02 |
| 760.5813 | 1201 | 13.23 | 0.47 | 11.72 | 0.44 | 0.89 | 2.4E−02 |
| 174.1408 | 1203 | 3.49 | 0.13 | 3.98 | 0.17 | 1.14 | 2.5E−02 |
| 594.4858 | 1202 | 4.25 | 0.40 | 5.82 | 0.56 | 1.37 | 2.6E−02 |
| 962.7618 | 1204 | 2.66 | 0.13 | 4.16 | 0.46 | 1.56 | 2.7E−02 |
| 826.5555 | 1102 | 2.14 | 0.17 | 5.70 | 1.87 | 2.67 | 2.8E−02 |
| 876.7233 | 1203 | 3.47 | 0.25 | 4.96 | 0.61 | 1.43 | 2.8E−02 |
| 302.2219 | 1201 | 13.90 | 1.45 | 18.90 | 1.71 | 1.36 | 2.9E−02 |
| 604.5431 | 1203 | 36.62 | 3.98 | 25.17 | 3.15 | 0.69 | 3.0E−02 |
| 792.5522 | 1204 | 4.37 | 0.58 | 7.20 | 0.93 | 1.65 | 3.1E−02 |
| 777.5689 | 1204 | 4.49 | 0.25 | 5.68 | 0.48 | 1.27 | 3.2E−02 |
| 946.8169 | 1204 | 6.59 | 0.70 | 4.49 | 0.63 | 0.68 | 3.2E−02 |
| 597.5053 | 1204 | 3.54 | 0.30 | 4.54 | 0.34 | 1.28 | 3.2E−02 |
| 766.5359 | 1204 | 2.92 | 0.15 | 4.77 | 1.06 | 1.63 | 3.2E−02 |
| 892.7708 | 1204 | 39.04 | 2.67 | 30.96 | 2.51 | 0.79 | 3.3E−02 |
| 605.5462 | 1203 | 14.99 | 1.68 | 10.28 | 1.31 | 0.69 | 3.3E−02 |
| 860.7753 | 1203 | 6.00 | 0.48 | 4.59 | 0.42 | 0.76 | 3.4E−02 |
| 592.4705 | 1204 | 2.70 | 0.15 | 3.46 | 0.30 | 1.28 | 3.4E−02 |
| 863.7358 | 1204 | 12.95 | 1.01 | 9.54 | 1.21 | 0.74 | 3.4E−02 |
| 920.8001 | 1204 | 10.52 | 1.02 | 7.72 | 0.77 | 0.73 | 3.6E−02 |
| 249.8832 | 1102 | 6.12 | 0.13 | 6.60 | 0.18 | 1.08 | 3.6E−02 |
| 805.5608 | 1101 | 4.42 | 0.21 | 5.14 | 0.27 | 1.16 | 3.7E−02 |
| 759.5781 | 1201 | 28.60 | 1.02 | 25.52 | 1.03 | 0.89 | 3.8E−02 |
| 242.2033 | 1203 | 5.30 | 0.18 | 5.94 | 0.25 | 1.12 | 3.9E−02 |
| 749.5371 | 1204 | 9.02 | 1.01 | 13.85 | 2.07 | 1.54 | 3.9E−02 |
| 856.6691 | 1102 | 8.16 | 0.26 | 9.16 | 0.41 | 1.12 | 4.0E−02 |
| 919.7934 | 1204 | 22.85 | 1.99 | 17.18 | 1.79 | 0.75 | 4.0E−02 |
| 728.5573 | 1204 | 3.12 | 0.24 | 3.92 | 0.29 | 1.26 | 4.0E−02 |
| 826.5563 | 1202 | 2.25 | 0.19 | 5.37 | 1.71 | 2.38 | 4.1E−02 |
| 562.4959 | 1203 | 5.62 | 0.48 | 4.22 | 0.45 | 0.75 | 4.2E−02 |
| 782.5645 | 1201 | 33.97 | 1.03 | 30.81 | 1.13 | 0.91 | 4.3E−02 |
| 776.5559 | 1204 | 3.15 | 0.19 | 4.92 | 0.66 | 1.56 | 4.3E−02 |
| 576.5117 | 1203 | 208.21 | 13.70 | 167.71 | 13.99 | 0.81 | 4.4E−02 |
| 362.0842 | 1201 | 1.95 | 0.01 | 2.11 | 0.06 | 1.08 | 4.4E−02 |
| 950.7566 | 1204 | 4.70 | 0.28 | 5.88 | 0.51 | 1.25 | 4.4E−02 |
| 876.7429 | 1204 | 7.66 | 0.61 | 5.93 | 0.57 | 0.77 | 4.6E−02 |
| 577.5154 | 1203 | 84.74 | 5.75 | 68.18 | 5.88 | 0.80 | 4.9E−02 |

TABLE 3

Molecular formula, accurate mass, and LC-MS/MS parameters for phosphatidylethanolamine (PtdEtn) metabolites with saturated fatty acids at the sn-2 position.

| Metabolite Name | Molecular Formula | Parent Mass | M-H Mass | Diagnostic Fragment Mass | MS/MS Transition |
|---|---|---|---|---|---|
| PtdEtn 16:0/18:0 | C39H78N1O8P1 | 719.5465 | 718.5 | R1 (C16H31O2)-255 | 718.5/255.2 |
| PtdEtn 16:0/20:0 | C41H82N1O8P1 | 747.5778 | 746.6 | R1 (C16H31O2)-255 | 746.6/255.2 |
| PtdEtn 16:0/22:0 | C43H86N1O8P1 | 775.6091 | 774.6 | R1 (C16H31O2)-255 | 774.6/255.2 |
| PtdEtn 16:0/24:0 | C45H90N1O8P1 | 803.6404 | 802.6 | R1 (C16H31O2)-255 | 802.6/255.2 |
| PtdEtn 16:0/26:0 | C47H94N1O8P1 | 831.6717 | 830.7 | R1 (C16H31O2)-255 | 830.7/255.2 |
| PtdEtn 16:0/28:0 | C49H98N1O8P1 | 859.7030 | 858.7 | R1 (C16H31O2)-255 | 858.7/255.2 |
| PtdEtn 16:0/30:0 | C51H102N1O8P1 | 887.7343 | 886.7 | R1 (C16H31O2)-255 | 886.7/255.2 |
| PtdEtn 16:0/32:0 | C53H106N1O8P1 | 915.7656 | 914.8 | R1 (C16H31O2)-255 | 914.8/255.2 |
| PtdEtn 16:0/34:0 | C55H110N1O8P1 | 943.7969 | 942.8 | R1 (C16H31O2)-255 | 942.8/255.2 |
| PtdEtn 16:0/36:0 | C57H114N1O8P1 | 971.8282 | 970.8 | R1 (C16H31O2)-255 | 970.8/255.2 |
| PtdEtn 16:0/38:0 | C59H118N1O8P1 | 999.8595 | 998.9 | R1 (C16H31O2)-255 | 998.9/255.2 |
| PtdEtn 16:0/40:0 | C61H122N1O8P1 | 1027.8908 | 1026.9 | R1 (C16H31O2)-255 | 1026.9/255.2 |
| PtdEtn 18:0/18:0 | C41H82N1O8P1 | 747.5778 | 746.6 | R1 (C18H35O2)-283 | 746.6/283.2 |
| PtdEtn 18:0/20:0 | C43H86N1O8P1 | 775.6091 | 774.6 | R1 (C18H35O2)-283 | 774.6/283.2 |
| PtdEtn 18:0/22:0 | C45H90N1O8P1 | 803.6404 | 802.6 | R1 (C18H35O2)-283 | 802.6/283.2 |
| PtdEtn 18:0/24:0 | C47H94N1O8P1 | 831.6717 | 830.7 | R1 (C18H35O2)-283 | 830.7/283.2 |
| PtdEtn 18:0/26:0 | C49H98N1O8P1 | 859.7030 | 858.7 | R1 (C18H35O2)-283 | 858.7/283.2 |
| PtdEtn 18:0/28:0 | C51H102N1O8P1 | 887.7343 | 886.7 | R1 (C18H35O2)-283 | 886.7/283.2 |
| PtdEtn 18:0/30:0 | C53H106N1O8P1 | 915.7656 | 914.8 | R1 (C18H35O2)-283 | 914.8/283.2 |
| PtdEtn 18:0/32:0 | C55H110N1O8P1 | 943.7969 | 942.8 | R1 (C18H35O2)-283 | 942.8/283.2 |
| PtdEtn 18:0/34:0 | C57H114N1O8P1 | 971.8282 | 970.8 | R1 (C18H35O2)-283 | 970.8/283.2 |
| PtdEtn 18:0/36:0 | C59H118N1O8P1 | 999.8595 | 998.9 | R1 (C18H35O2)-283 | 998.9/283.2 |
| PtdEtn 18:0/38:0 | C61H122N1O8P1 | 1027.8908 | 1026.9 | R1 (C18H35O2)-283 | 1026.9/283.2 |
| PtdEtn 18:0/40:0 | C63H126N1O8P1 | 1055.9221 | 1054.9 | R1 (C18H35O2)-283 | 1054.9/283.2 |

TABLE 4

Molecular formula, accurate mass, and LC-MS/MS parameters for phosphatidylethanolamine (PtdEtn) metabolites with sn-2 position fatty acids containing one unsaturation.

| Metabolite Name | Molecular Formula | Parent Mass | M-H Mass | Diagnostic Fragment Mass | MS/MS Transition |
|---|---|---|---|---|---|
| PtdEtn 16:0/18:1 | C39H76N1O8P1 | 717.5308 | 716.5 | R1 (C16H31O2)-255 | 716.5/255.2 |
| PtdEtn 16:0/20:1 | C41H80N1O8P1 | 745.5621 | 744.6 | R1 (C16H31O2)-255 | 744.6/255.2 |
| PtdEtn 16:0/22:1 | C43H84N1O8P1 | 773.5934 | 772.6 | R1 (C16H31O2)-255 | 772.6/255.2 |
| PtdEtn 16:0/24:1 | C45H88N1O8P1 | 801.6247 | 800.6 | R1 (C16H31O2)-255 | 800.6/255.2 |
| PtdEtn 16:0/26:1 | C47H92N1O8P1 | 829.6560 | 828.6 | R1 (C16H31O2)-255 | 828.6/255.2 |
| PtdEtn 16:0/28:1 | C49H96N1O8P1 | 857.6873 | 856.7 | R1 (C16H31O2)-255 | 856.7/255.2 |
| PtdEtn 16:0/30:1 | C51H100N1O8P1 | 885.7186 | 884.7 | R1 (C16H31O2)-255 | 884.7/255.2 |
| PtdEtn 16:0/32:1 | C53H104N1O8P1 | 913.7499 | 912.7 | R1 (C16H31O2)-255 | 912.7/255.2 |
| PtdEtn 16:0/34:1 | C55H108N1O8P1 | 941.7812 | 940.8 | R1 (C16H31O2)-255 | 940.8//255.2 |
| PtdEtn 16:0/36:1 | C57H112N1O8P1 | 969.8125 | 968.8 | R1 (C16H31O2)-255 | 968.8/255.2 |
| PtdEtn 16:0/38:1 | C59H116N1O8P1 | 997.8438 | 996.8 | R1 (C16H31O2)-255 | 996.8/255.2 |
| PtdEtn 16:0/40:1 | C61H120N1O8P1 | 1025.8751 | 1024.9 | R1 (C16H31O2)-255 | 1024.9/255.2 |
| PtdEtn 18:0/18:1 | C41H80N1O8P1 | 1053.9064 | 1052.9 | R1 (C18H35O2)-283 | 744.6/283.2 |
| PtdEtn 18:0/20:1 | C43H84N1O8P1 | 773.5934 | 772.6 | R1 (C18H35O2)-283 | 772.6/283.2 |
| PtdEtn 18:0/22:1 | C45H88N1O8P1 | 801.6247 | 800.6 | R1 (C18H35O2)-283 | 800.6/283.2 |
| PtdEtn 18:0/24:1 | C47H92N1O8P1 | 829.6560 | 828.6 | R1 (C18H35O2)-283 | 828.6/283.2 |
| PtdEtn 18:0/26:1 | C49H96N1O8P1 | 857.6873 | 856.7 | R1 (C18H35O2)-283 | 856.7/283.2 |
| PtdEtn 18:0/28:1 | C51H100N1O8P1 | 885.7186 | 884.7 | R1 (C18H35O2)-283 | 884.7/283.2 |
| PtdEtn 18:0/30:1 | C53H104N1O8P1 | 913.7499 | 912.7 | R1 (C18H35O2)-283 | 912.7/283.2 |
| PtdEtn 18:0/32:1 | C55H108N1O8P1 | 941.7812 | 940.8 | R1 (C18H35O2)-283 | 940.8/283.2 |
| PtdEtn 18:0/34:1 | C57H112N1O8P1 | 969.8125 | 968.8 | R1 (C18H35O2)-283 | 968.8/283.2 |
| PtdEtn 18:0/36:1 | C59H116N1O8P1 | 997.8438 | 996.8 | R1 (C18H35O2)-283 | 996.8/283.2 |
| PtdEtn 18:0/38:1 | C61H120N1O8P1 | 1025.8751 | 1024.9 | R1 (C18H35O2)-283 | 1024.9/283.2 |
| PtdEtn 18:0/40:1 | C63H124N1O8P1 | 1053.9064 | 1052.9 | R1 (C18H35O2)-283 | 1052.9/283.2 |

TABLE 5

Molecular formula, accurate mass, and LC-MS/MS parameters for phosphatidylethanolamine (PtdEtn) metabolites with sn-2 position fatty acids containing two unsaturations.

| Metabolite Name | Molecular Formula | Parent Mass | M-H Mass | Diagnostic Fragment Mass | MS/MS Transition |
|---|---|---|---|---|---|
| PtdEtn 16:0/18:2 | C39H74N1O8P1 | 715.5152 | 714.5 | R1 (C16H31O2)-255 | 714.5/255.2 |
| PtdEtn 16:0/20:2 | C41H78N1O8P1 | 743.5465 | 742.5 | R1 (C16H31O2)-255 | 742.5/255.2 |
| PtdEtn 16:0/22:2 | C43H82N1O8P1 | 771.5778 | 770.6 | R1 (C16H31O2)-255 | 770.6/255.2 |
| PtdEtn 16:0/24:2 | C45H86N1O8P1 | 799.6091 | 798.6 | R1 (C16H31O2)-255 | 798.6/255.2 |
| PtdEtn 16:0/26:2 | C47H90N1O8P1 | 827.6404 | 826.6 | R1 (C16H31O2)-255 | 826.6/255.2 |
| PtdEtn 16:0/28:2 | C49H94N1O8P1 | 855.6717 | 854.7 | R1 (C16H31O2)-255 | 854.7/255.2 |
| PtdEtn 16:0/30:2 | C51H98N1O8P1 | 883.7030 | 882.7 | R1 (C16H31O2)-255 | 882.7/255.2 |
| PtdEtn 16:0/32:2 | C53H102N1O8P1 | 911.7343 | 910.7 | R1 (C16H31O2)-255 | 910.7/255.2 |
| PtdEtn 16:0/34:2 | C55H106N1O8P1 | 939.7656 | 938.8 | R1 (C16H31O2)-255 | 938.8/255.2 |
| PtdEtn 16:0/36:2 | C57H110N1O8P1 | 967.7969 | 966.8 | R1 (C16H31O2)-255 | 966.8/255.2 |
| PtdEtn 16:0/38:2 | C59H114N1O8P1 | 995.8282 | 994.8 | R1 (C16H31O2)-255 | 994.8/255.2 |
| PtdEtn 16:0/40:2 | C61H118N1O8P1 | 1023.8595 | 1022.9 | R1 (C16H31O2)-255 | 1022.9/255.2 |
| PtdEtn 18:0/18:2 | C41H78N1O8P1 | 743.5465 | 742.5 | R1 (C18H35O2)-283 | 742.5/283.2 |
| PtdEtn 18:0/20:2 | C43H82N1O8P1 | 771.5778 | 770.6 | R1 (C18H35O2)-283 | 770.6/283.2 |
| PtdEtn 18:0/22:2 | C45H86N1O8P1 | 799.6091 | 798.6 | R1 (C18H35O2)-283 | 798.6/283.2 |
| PtdEtn 18:0/24:2 | C47H90N1O8P1 | 827.6404 | 826.6 | R1 (C18H35O2)-283 | 826.6/283.2 |
| PtdEtn 18:0/26:2 | C49H94N1O8P1 | 855.6717 | 854.7 | R1 (C18H35O2)-283 | 854.7/283.2 |
| PtdEtn 18:0/28:2 | C51H98N1O8P1 | 883.7030 | 882.7 | R1 (C18H35O2)-283 | 882.7/283.2 |
| PtdEtn 18:0/30:2 | C53H102N1O8P1 | 911.7343 | 910.7 | R1 (C18H35O2)-283 | 910.7/283.2 |
| PtdEtn 18:0/32:2 | C55H106N1O8P1 | 939.7656 | 938.8 | R1 (C18H35O2)-283 | 938.8/283.2 |
| PtdEtn 18:0/34:2 | C57H110N1O8P1 | 967.7969 | 966.8 | R1 (C18H35O2)-283 | 966.8/283.2 |
| PtdEtn 18:0/36:2 | C59H114N1O8P1 | 995.8282 | 994.8 | R1 (C18H35O2)-283 | 994.8/283.2 |
| PtdEtn 18:0/38:2 | C61H118N1O8P1 | 1023.8595 | 1022.9 | R1 (C18H35O2)-283 | 1022.9/283.2 |
| PtdEtn 18:0/40:2 | C63H122N1O8P1 | 1051.8908 | 1050.9 | R1 (C18H35O2)-283 | 1050.9/283.2 |

TABLE 6

Molecular formula, accurate mass, and LC-MS/MS parameters for phosphatidylethanolamine (PtdEtn) metabolites with sn-2 position fatty acids containing three unsaturations.

| Metabolite Name | Molecular Formula | Parent Mass | M-H Mass | Diagnostic Fragment Mass | MS/MS Transition |
|---|---|---|---|---|---|
| PtdEtn 16:0/18:3 | C39H72N1O8P1 | 713.4995 | 712.5 | R1 (C16H31O2)-255 | 712.5/255.2 |
| PtdEtn 16:0/20:3 | C41H76N1O8P1 | 741.5308 | 740.5 | R1 (C16H31O2)-255 | 740.5/255.2 |
| PtdEtn 16:0/22:3 | C43H80N1O8P1 | 769.5621 | 768.6 | R1 (C16H31O2)-255 | 768.6/255.2 |

TABLE 6-continued

Molecular formula, accurate mass, and LC-MS/MS parameters for phosphatidylethanolamine (PtdEtn) metabolites with sn-2 position fatty acids containing three unsaturations.

| Metabolite Name | Molecular Formula | Parent Mass | M-H Mass | Diagnostic Fragment Mass | MS/MS Transition |
|---|---|---|---|---|---|
| PtdEtn 16:0/24:3 | C45H84N1O8P1 | 797.5934 | 796.6 | R1 (C16H31O2)-255 | 796.6/255.2 |
| PtdEtn 16:0/26:3 | C47H88N1O8P1 | 825.6247 | 824.6 | R1 (C16H31O2)-255 | 824.6/255.2 |
| PtdEtn 16:0/28:3 | C49H92N1O8P1 | 853.6560 | 852.6 | R1 (C16H31O2)-255 | 852.6/255.2 |
| PtdEtn 16:0/30:3 | C51H96N1O8P1 | 881.6873 | 880.7 | R1 (C16H31O2)-255 | 880.7/255.2 |
| PtdEtn 16:0/32:3 | C53H100N1O8P1 | 909.7186 | 908.7 | R1 (C16H31O2)-255 | 908.7/255.2 |
| PtdEtn 16:0/34:3 | C55H104N1O8P1 | 937.7499 | 936.7 | R1 (C16H31O2)-255 | 936.7/255.2 |
| PtdEtn 16:0/36:3 | C57H108N1O8P1 | 965.7812 | 964.8 | R1 (C16H31O2)-255 | 964.8/255.2 |
| PtdEtn 16:0/38:3 | C59H112N1O8P1 | 993.8125 | 992.8 | R1 (C16H31O2)-255 | 992.8/255.2 |
| PtdEtn 16:0/40:3 | C61H116N1O8P1 | 1021.8438 | 1020.8 | R1 (C16H31O2)-255 | 1020.8/255.2 |
| PtdEtn 18:0/18:3 | C41H76N1O8P1 | 741.5308 | 740.5 | R1 (C18H35O2)-283 | 740.5/283.2 |
| PtdEtn 18:0/20:3 | C43H80N1O8P1 | 769.5621 | 768.6 | R1 (C18H35O2)-283 | 768.6/283.2 |
| PtdEtn 18:0/22:3 | C45H84N1O8P1 | 797.5934 | 796.6 | R1 (C18H35O2)-283 | 796.6/283.2 |
| PtdEtn 18:0/24:3 | C47H88N1O8P1 | 825.6247 | 824.6 | R1 (C18H35O2)-283 | 824.6/283.2 |
| PtdEtn 18:0/26:3 | C49H92N1O8P1 | 853.6560 | 852.6 | R1 (C18H35O2)-283 | 852.6/283.2 |
| PtdEtn 18:0/28:3 | C51H96N1O8P1 | 881.6873 | 880.7 | R1 (C18H35O2)-283 | 880.7/283.2 |
| PtdEtn 18:0/30:3 | C53H100N1O8P1 | 909.7186 | 908.7 | R1 (C18H35O2)-283 | 908.7/283.2 |
| PtdEtn 18:0/32:3 | C55H104N1O8P1 | 937.7499 | 936.7 | R1 (C18H35O2)-283 | 936.7/283.2 |
| PtdEtn 18:0/34:3 | C57H108N1O8P1 | 965.7812 | 964.8 | R1 (C18H35O2)-283 | 964.8/283.2 |
| PtdEtn 18:0/36:3 | C59H112N1O8P1 | 993.8125 | 992.8 | R1 (C18H35O2)-283 | 992.8/283.2 |
| PtdEtn 18:0/38:3 | C61H116N1O8P1 | 1021.8438 | 1020.8 | R1 (C18H35O2)-283 | 1020.8/283.2 |
| PtdEtn 18:0/40:3 | C63H120N1O8P1 | 1049.8751 | 1048.9 | R1 (C18H35O2)-283 | 1048.9/283.2 |

TABLE 7

Molecular formula, accurate mass, and LC-MS/MS parameters for phosphatidylethanolamine (PtdEtn) metabolites with sn-2 position fatty acids containing four unsaturations.

| Metabolite Name | Molecular Formula | Parent Mass | M-H Mass | Diagnostic Fragment Mass | MS/MS Transition |
|---|---|---|---|---|---|
| PtdEtn 16:0/20:4 | C41H74N1O8P1 | 739.5152 | 738.5 | R1 (C16H31O2)-255 | 738.5/255.2 |
| PtdEtn 16:0/22:4 | C43H78N1O8P1 | 767.5465 | 766.5 | R1 (C16H31O2)-255 | 766.5/255.2 |
| PtdEtn 16:0/24:4 | C45H82N1O8P1 | 795.5778 | 794.6 | R1 (C16H31O2)-255 | 794.6/255.2 |
| PtdEtn 16:0/26:4 | C47H86N1O8P1 | 823.6091 | 822.6 | R1 (C16H31O2)-255 | 822.6/255.2 |
| PtdEtn 16:0/28:4 | C49H90N1O8P1 | 851.6404 | 850.6 | R1 (C16H31O2)-255 | 850.6/255.2 |
| PtdEtn 16:0/30:4 | C51H94N1O8P1 | 879.6717 | 878.7 | R1 (C16H31O2)-255 | 878.7/255.2 |
| PtdEtn 16:0/32:4 | C53H98N1O8P1 | 907.7030 | 906.7 | R1 (C16H31O2)-255 | 906.7/255.2 |
| PtdEtn 16:0/34:4 | C55H102N1O8P1 | 935.7343 | 934.7 | R1 (C16H31O2)-255 | 934.7/255.2 |
| PtdEtn 16:0/36:4 | C57H106N1O8P1 | 963.7656 | 962.8 | R1 (C16H31O2)-255 | 962.8/255.2 |
| PtdEtn 16:0/38:4 | C59H110N1O8P1 | 991.7969 | 990.8 | R1 (C16H31O2)-255 | 990.8/255.2 |
| PtdEtn 16:0/40:4 | C61H114N1O8P1 | 1019.8282 | 1018.8 | R1 (C16H31O2)-255 | 1018.8/255.2 |
| PtdEtn 18:0/20:4 | C43H78N1O8P1 | 767.5465 | 766.5 | R1 (C18H35O2)-283 | 766.5/283.2 |
| PtdEtn 18:0/22:4 | C45H82N1O8P1 | 795.5778 | 794.6 | R1 (C18H35O2)-283 | 794.6/283.2 |
| PtdEtn 18:0/24:4 | C47H86N1O8P1 | 823.6091 | 822.6 | R1 (C18H35O2)-283 | 822.6/283.2 |
| PtdEtn 18:0/26:4 | C49H90N1O8P1 | 851.6404 | 850.6 | R1 (C18H35O2)-283 | 850.6/283.2 |
| PtdEtn 18:0/28:4 | C51H94N1O8P1 | 879.6717 | 878.7 | R1 (C18H35O2)-283 | 878.7/283.2 |
| PtdEtn 18:0/30:4 | C53H98N1O8P1 | 907.7030 | 906.7 | R1 (C18H35O2)-283 | 906.7/283.2 |
| PtdEtn 18:0/32:4 | C55H102N1O8P1 | 935.7343 | 934.7 | R1 (C18H35O2)-283 | 934.7/283.2 |
| PtdEtn 18:0/34:4 | C57H106N1O8P1 | 963.7656 | 962.8 | R1 (C18H35O2)-283 | 962.8/283.2 |
| PtdEtn 18:0/36:4 | C59H110N1O8P1 | 991.7969 | 990.8 | R1 (C18H35O2)-283 | 990.8/283.2 |
| PtdEtn 18:0/38:4 | C61H114N1O8P1 | 1019.8282 | 1018.8 | R1 (C18H35O2)-283 | 1018.8/283.2 |
| PtdEtn 18:0/40:4 | C63H118N1O8P1 | 1047.8595 | 1046.9 | R1 (C18H35O2)-283 | 1046.9/283.2 |

TABLE 8

Molecular formula, accurate mass, and LC-MS/MS parameters for phosphatidylethanolamine (PtdEtn) metabolites with sn-2 position fatty acids containing five unsaturations.

| Metabolite Name | Molecular Formula | Parent Mass | M-H Mass | Diagnostic Fragment Mass | MS/MS Transition |
|---|---|---|---|---|---|
| PtdEtn 16:0/20:5 | C41H72N1O8P1 | 737.4995 | 736.5 | R1 (C16H31O2)-255 | 736.5/255.2 |
| PtdEtn 16:0/22:5 | C43H76N1O8P1 | 765.5308 | 764.5 | R1 (C16H31O2)-255 | 764.5/255.2 |
| PtdEtn 16:0/24:5 | C45H80N1O8P1 | 793.5621 | 792.6 | R1 (C16H31O2)-255 | 792.6/255.2 |
| PtdEtn 16:0/26:5 | C47H84N1O8P1 | 821.5934 | 820.6 | R1 (C16H31O2)-255 | 820.6/255.2 |
| PtdEtn 16:0/28:5 | C49H88N1O8P1 | 849.6247 | 848.6 | R1 (C16H31O2)-255 | 848.6/255.2 |
| PtdEtn 16:0/30:5 | C51H92N1O8P1 | 877.6560 | 876.6 | R1 (C16H31O2)-255 | 876.6/255.2 |
| PtdEtn 16:0/32:5 | C53H96N1O8P1 | 905.6873 | 904.7 | R1 (C16H31O2)-255 | 904.7/255.2 |
| PtdEtn 16:0/34:5 | C55H100N1O8P1 | 933.7186 | 932.7 | R1 (C16H31O2)-255 | 932.7/255.2 |

TABLE 8-continued

Molecular formula, accurate mass, and LC-MS/MS parameters for phosphatidylethanolamine (PtdEtn) metabolites with sn-2 position fatty acids containing five unsaturations.

| Metabolite Name | Molecular Formula | Parent Mass | M-H Mass | Diagnostic Fragment Mass | MS/MS Transition |
|---|---|---|---|---|---|
| PtdEtn 16:0/36:5 | C57H104N1O8P1 | 961.7499 | 960.7 | R1 (C16H31O2)-255 | 960.7/255.2 |
| PtdEtn 16:0/38:5 | C59H108N1O8P1 | 989.7812 | 988.8 | R1 (C16H31O2)-255 | 988.8/255.2 |
| PtdEtn 16:0/40:5 | C61H112N1O8P1 | 1017.8125 | 1016.8 | R1 (C16H31O2)-255 | 1016.8/255.2 |
| PtdEtn 18:0/20:5 | C43H76N1O8P1 | 765.5308 | 764.5 | R1 (C18H35O2)-283 | 764.5/283.2 |
| PtdEtn 18:0/22:5 | C45H80N1O8P1 | 793.5621 | 792.6 | R1 (C18H35O2)-283 | 792.6/283.2 |
| PtdEtn 18:0/24:5 | C47H84N1O8P1 | 821.5934 | 820.6 | R1 (C18H35O2)-283 | 820.6/283.2 |
| PtdEtn 18:0/26:5 | C49H88N1O8P1 | 849.6247 | 848.6 | R1 (C18H35O2)-283 | 848.6/283.2 |
| PtdEtn 18:0/28:5 | C51H92N1O8P1 | 877.6560 | 876.6 | R1 (C18H35O2)-283 | 876.6/283.2 |
| PtdEtn 18:0/30:5 | C53H96N1O8P1 | 905.6873 | 904.7 | R1 (C18H35O2)-283 | 904.7/283.2 |
| PtdEtn 18:0/32:5 | C55H100N1O8P1 | 933.7186 | 932.7 | R1 (C18H35O2)-283 | 932.7/283.2 |
| PtdEtn 18:0/34:5 | C57H104N1O8P1 | 961.7499 | 960.7 | R1 (C18H35O2)-283 | 960.7/283.2 |
| PtdEtn 18:0/36:5 | C59H108N1O8P1 | 989.7812 | 988.8 | R1 (C18H35O2)-283 | 988.8/283.2 |
| PtdEtn 18:0/38:5 | C61H112N1O8P1 | 1017.8125 | 1016.8 | R1 (C18H35O2)-283 | 1016.8/283.2 |
| PtdEtn 18:0/40:5 | C63H116N1O8P1 | 1045.8438 | 1044.8 | R1 (C18H35O2)-283 | 1044.8/283.2 |

TABLE 9

Molecular formula, accurate mass, and LC-MS/MS parameters for phosphatidylethanolamine (PtdEtn) metabolites with sn-2 position fatty acids containing six unsaturations.

| Metabolite Name | Molecular Formula | Parent Mass | M-H Mass | Diagnostic Fragment Mass | MS/MS Transition |
|---|---|---|---|---|---|
| PtdEtn 16:0/20:6 | C41H70N1O8P1 | 735.4839 | 734.5 | R1 (C16H31O2)-255 | 734.5/255.2 |
| PtdEtn 16:0/22:6 | C43H74N1O8P1 | 763.5152 | 762.5 | R1 (C16H31O2)-255 | 762.5/255.2 |
| PtdEtn 16:0/24:6 | C45H78N1O8P1 | 791.5465 | 790.5 | R1 (C16H31O2)-255 | 790.5/255.2 |
| PtdEtn 16:0/26:6 | C47H82N1O8P1 | 819.5778 | 818.6 | R1 (C16H31O2)-255 | 818.6/255.2 |
| PtdEtn 16:0/28:6 | C49H86N1O8P1 | 847.6091 | 846.6 | R1 (C16H31O2)-255 | 846.6/255.2 |
| PtdEtn 16:0/30:6 | C51H90N1O8P1 | 875.6404 | 874.6 | R1 (C16H31O2)-255 | 874.6/255.2 |
| PtdEtn 16:0/32:6 | C53H94N1O8P1 | 903.6717 | 902.7 | R1 (C16H31O2)-255 | 902.7/255.2 |
| PtdEtn 16:0/34:6 | C55H98N1O8P1 | 931.7030 | 930.7 | R1 (C16H31O2)-255 | 930.7/255.2 |
| PtdEtn 16:0/36:6 | C57H102N1O8P1 | 959.7343 | 958.7 | R1 (C16H31O2)-255 | 958.7/255.2 |
| PtdEtn 16:0/38:6 | C59H106N1O8P1 | 987.7656 | 986.8 | R1 (C16H31O2)-255 | 986.8/255.2 |
| PtdEtn 16:0/40:6 | C61H110N1O8P1 | 1015.7969 | 1014.8 | R1 (C16H31O2)-255 | 1014.8/255.2 |
| PtdEtn 18:0/20:6 | C43H74N1O8P1 | 763.5152 | 762.5 | R1 (C18H35O2)-283 | 762.5/283.2 |
| PtdEtn 18:0/22:6 | C45H78N1O8P1 | 791.5465 | 790.5 | R1 (C18H35O2)-283 | 790.5/283.2 |
| PtdEtn 18:0/24:6 | C47H82N1O8P1 | 819.5778 | 818.6 | R1 (C18H35O2)-283 | 818.6/283.2 |
| PtdEtn 18:0/26:6 | C49H86N1O8P1 | 847.6091 | 846.6 | R1 (C18H35O2)-283 | 846.6/283.2 |
| PtdEtn 18:0/28:6 | C51H90N1O8P1 | 875.6404 | 874.6 | R1 (C18H35O2)-283 | 874.6/283.2 |
| PtdEtn 18:0/30:6 | C53H94N1O8P1 | 903.6717 | 902.7 | R1 (C18H35O2)-283 | 902.7/283.2 |
| PtdEtn 18:0/32:6 | C55H98N1O8P1 | 931.7030 | 930.7 | R1 (C18H35O2)-283 | 930.7/283.2 |
| PtdEtn 18:0/34:6 | C57H102N1O8P1 | 959.7343 | 958.7 | R1 (C18H35O2)-283 | 958.7/283.2 |
| PtdEtn 18:0/36:6 | C59H106N1O8P1 | 987.7656 | 986.8 | R1 (C18H35O2)-283 | 986.8/283.2 |
| PtdEtn 18:0/38:6 | C61H110N1O8P1 | 1015.7969 | 1014.8 | R1 (C18H35O2) - 283 | 1014.8/283.2 |
| PtdEtn 18:0/40:6 | C63H114N1O8P1 | 1043.8282 | 1042.8 | R1 (C18H35O2) - 283 | 1042.8/283.2 |

TABLE 10

Molecular formula, accurate mass, and LC-MS/MS parameters for ethanolamine plasmalogens (PlsEtn) metabolites with selected sn-2 position fatty acids.

| Metabolite Name | Molecular Formula | Parent Mass | M-H Mass | Diagnostic Fragment Mass | MS/MS Transition |
|---|---|---|---|---|---|
| PlsEtn 16:0/18:1 | C39H76N1O7P1 | 701.5359 | 700.5 | R2 (C18H33O2)-281 | 700.5/281.2 |
| PlsEtn 16:0/18:2 | C39H74N1O7P1 | 699.5203 | 698.5 | R2 (C18H31O2)-279 | 698.5/279.2 |
| PlsEtn 16:0/18:3 | C39H72N1O7P1 | 697.5046 | 696.5 | R2 (C18H29O2)-277 | 696.5/277.2 |
| PlsEtn 16:0/20:4 | C41H74N1O7P1 | 723.5203 | 722.5 | R2 (C20H31O2)-303 | 722.5/303.2 |
| PlsEtn 16:0/22:6 | C43H74N1O7P1 | 747.5203 | 746.5 | R2 (C22H31O2)-327 | 746.5/327.2 |
| PlsEtn 18:0/18:1 | C41H80N1O7P1 | 729.5672 | 728.5 | R2 (C18H33O2)-281 | 728.5/281.2 |
| PlsEtn 18:0/18:2 | C41H78N1O7P1 | 727.5516 | 726.5 | R2 (C18H31O2)-279 | 726.5/279.2 |
| PlsEtn 18:0/18:3 | C41H76N1O7P1 | 725.5359 | 724.5 | R2 (C18H29O2)-277 | 724.5/277.2 |
| PlsEtn 18:0/20:4 | C43H78N1O7P1 | 751.5516 | 750.5 | R2 (C20H31O2)-303 | 750.5/303.2 |
| PlsEtn 18:0/22:6 | C45H78N1O7P1 | 775.5516 | 774.5 | R2 (C22H31O2)-327 | 774.5/327.2 |
| PlsEtn 18:1/18:1 | C41H78N1O7P1 | 727.5516 | 726.5 | R2 (C18H33O2)-281 | 726.5/281.2 |
| PlsEtn 18:1/18:2 | C41H76N1O7P1 | 725.5359 | 724.5 | R2 (C18H31O2)-279 | 724.5/279.2 |
| PlsEtn 18:1/18:3 | C41H74N1O7P1 | 723.5203 | 722.5 | R2 (C18H29O2)-277 | 722.5/277.2 |
| PlsEtn 18:1/20:4 | C43H76N1O7P1 | 749.5359 | 748.5 | R2 (C20H31O2)-303 | 748.5/303.2 |
| PlsEtn 18:1/22:6 | C45H76N1O7P1 | 773.5359 | 772.5 | R2 (C22H31O2)-327 | 772.5/327.2 |

TABLE 11

Plasma levels of phosphatidylethanolamine (PtdEtn) metabolites with saturated fatty acids at the sn-2 position in non-autistic children, autistic children not taking carnitine supplements, and autistic children taking carnitine supplements (All values are expressed as the ratio to PtdEtn 16:0/18:0).

| Metabolite Name | MS/MS Transition | Control Avg | Control SEM | Autism −Carnitine Avg | Autism −Carnitine SEM | Autism +Carnitine Avg | Autism +Carnitine SEM | Autism vs. Control −Carnitine Ratio | Autism vs. Control −Carnitine p | Autism vs. Control +Carnitine Ratio | Autism vs. Control +Carnitine p | +Carn vs. −Carn Ratio | +Carn vs. −Carn p |
|---|---|---|---|---|---|---|---|---|---|---|---|---|---|
| PtdEtn 16:0/18:0 | 718.5/255.2 | 1.000 | 0.000 | 1.000 | 0.000 | 1.000 | 0.000 | 1.00 | 1.0E+00 | 1.00 | 1.0E+00 | 1.00 | 1.0E+00 |
| PtdEtn 16:0/20:0 | 746.6/255.2 | 0.694 | 0.019 | 0.703 | 0.013 | 0.734 | 0.036 | 1.01 | 6.9E−01 | 1.06 | 2.8E−01 | 1.04 | 3.2E−01 |
| PtdEtn 16:0/22:0 | 774.6/255.2 | 0.030 | 0.001 | 0.036 | 0.002 | 0.032 | 0.002 | 1.19 | 6.2E−03 | 1.05 | 5.3E−01 | 0.88 | 1.6E−01 |
| PtdEtn 16:0/24:0 | 802.6/255.2 | 0.033 | 0.001 | 0.041 | 0.001 | 0.034 | 0.001 | 1.27 | 9.8E−06 | 1.04 | 5.3E−01 | 0.82 | 3.9E−03 |
| PtdEtn 16:0/26:0 | 830.7/255.2 | 0.044 | 0.003 | 0.053 | 0.003 | 0.050 | 0.005 | 1.21 | 5.2E−02 | 1.13 | 3.6E−01 | 0.93 | 5.8E−01 |
| PtdEtn 16:0/28:0 | 858.7/255.2 | 0.054 | 0.003 | 0.092 | 0.008 | 0.056 | 0.005 | 1.70 | 3.8E−05 | 1.03 | 7.9E−01 | 0.61 | 8.7E−03 |
| PtdEtn 16:0/30:0 | 886.7/255.2 | 0.009 | 0.000 | 0.009 | 0.000 | 0.011 | 0.001 | 1.08 | 2.8E−01 | 1.27 | 1.7E−02 | 1.18 | 7.8E−02 |
| PtdEtn 16:0/32:0 | 914.8/255.2 | 0.004 | 0.000 | 0.005 | 0.000 | 0.006 | 0.000 | 1.20 | 8.2E−02 | 1.27 | 4.7E−02 | 1.06 | 6.5E−01 |
| PtdEtn 16:0/34:0 | 942.8/255.2 | 0.004 | 0.000 | 0.005 | 0.000 | 0.005 | 0.001 | 1.24 | 9.7E−03 | 1.42 | 8.3E−03 | 1.14 | 2.1E−01 |
| PtdEtn 16:0/36:0 | 970.8/255.2 | 0.004 | 0.000 | 0.004 | 0.000 | 0.005 | 0.000 | 1.23 | 2.9E−02 | 1.33 | 1.3E−02 | 1.08 | 4.4E−01 |
| PtdEtn 16:0/38:0 | 998.9/255.2 | 0.004 | 0.000 | 0.005 | 0.000 | 0.005 | 0.000 | 1.28 | 2.3E−02 | 1.31 | 1.2E−02 | 1.02 | 9.0E−01 |
| PtdEtn 16:0/40:0 | 1026.9/255.2 | 0.005 | 0.000 | 0.005 | 0.000 | 0.006 | 0.001 | 1.11 | 1.7E−01 | 1.28 | 3.0E−02 | 1.15 | 2.1E−01 |
| PtdEtn 18:0/18:0 | 746.6/283.2 | 0.525 | 0.012 | 0.581 | 0.023 | 0.588 | 0.034 | 1.11 | 4.0E−02 | 1.12 | 2.9E−02 | 1.01 | 8.7E−01 |
| PtdEtn 18:0/20:0 | 774.6/283.2 | 0.427 | 0.017 | 0.578 | 0.033 | 0.491 | 0.041 | 1.35 | 2.3E−04 | 1.15 | 9.0E−02 | 0.85 | 1.6E−01 |
| PtdEtn 18:0/22:0 | 802.6/283.2 | 0.044 | 0.002 | 0.076 | 0.006 | 0.048 | 0.003 | 1.73 | 5.2E−06 | 1.09 | 3.2E−01 | 0.63 | 7.0E−03 |
| PtdEtn 18:0/24:0 | 830.7/283.2 | 0.026 | 0.001 | 0.038 | 0.002 | 0.028 | 0.002 | 1.48 | 1.0E−05 | 1.09 | 3.2E−01 | 0.74 | 8.7E−03 |
| PtdEtn 18:0/26:0 | 858.7/283.2 | 0.034 | 0.004 | 0.061 | 0.006 | 0.039 | 0.005 | 1.80 | 4.5E−04 | 1.13 | 5.4E−01 | 0.63 | 3.1E−02 |
| PtdEtn 18:0/28:0 | 886.7/283.2 | 0.031 | 0.002 | 0.056 | 0.005 | 0.036 | 0.004 | 1.83 | 2.4E−05 | 1.16 | 1.8E−01 | 0.64 | 2.5E−02 |
| PtdEtn 18:0/30:0 | 914.8/283.2 | 0.003 | 0.000 | 0.004 | 0.000 | 0.005 | 0.001 | 1.34 | 1.3E−02 | 1.49 | 5.2E−03 | 1.11 | 4.5E−01 |
| PtdEtn 18:0/32:0 | 942.8/283.2 | 0.002 | 0.000 | 0.002 | 0.000 | 0.002 | 0.000 | 1.10 | 4.9E−01 | 1.14 | 4.1E−01 | 1.04 | 8.3E−01 |
| PtdEtn 18:0/34:0 | 970.8/283.2 | 0.002 | 0.000 | 0.002 | 0.000 | 0.003 | 0.000 | 1.35 | 6.1E−02 | 1.72 | 3.6E−03 | 1.27 | 1.9E−01 |
| PtdEtn 18:0/36:0 | 998.9/283.2 | 0.002 | 0.000 | 0.002 | 0.000 | 0.003 | 0.000 | 1.22 | 1.3E−01 | 1.33 | 8.1E−02 | 1.09 | 6.1E−01 |
| PtdEtn 18:0/38:0 | 1026.9/283.2 | 0.002 | 0.000 | 0.003 | 0.000 | 0.003 | 0.000 | 1.63 | 2.0E−03 | 1.25 | 1.1E−01 | 0.77 | 2.3E−01 |
| PtdEtn 18:0/40:0 | 1054.9/283.2 | 0.003 | 0.000 | 0.003 | 0.000 | 0.003 | 0.001 | 1.32 | 6.3E−03 | 1.26 | 1.3E−01 | 0.95 | 7.3E−01 |

TABLE 12

Plasma levels of phosphatidylethanolamine (PtdEtn) metabolites with sn-2 position fatty acids containing one unsaturation in non-autistic children, autistic children not taking carnitine supplements, and autistic children taking carnitine supplements (All values are expressed as the ratio to PtdEtn 16:0/18:0).

| Metabolite Name | MS/MS Transition | Control Avg | Control SEM | Autism −Carnitine Avg | Autism −Carnitine SEM | Autism +Carnitine Avg | Autism +Carnitine SEM | Autism vs. Control −Carnitine Ratio | Autism vs. Control −Carnitine p | Autism vs. Control +Carnitine Ratio | Autism vs. Control +Carnitine p | +Carn vs. −Carn Ratio | +Carn vs. −Carn p |
|---|---|---|---|---|---|---|---|---|---|---|---|---|---|
| PtdEtn 16:0/18:1 | 716.5/255.2 | 0.633 | 0.026 | 0.497 | 0.022 | 0.860 | 0.093 | 0.79 | 1.9E−04 | 1.36 | 2.6E−03 | 1.73 | 2.0E−06 |
| PtdEtn 16:0/20:1 | 744.6/255.2 | 6.423 | 0.178 | 6.316 | 0.136 | 6.882 | 0.322 | 0.98 | 6.3E−01 | 1.07 | 1.9E−01 | 1.09 | 6.3E−02 |
| PtdEtn 16:0/22:1 | 772.6/255.2 | 0.080 | 0.002 | 0.087 | 0.002 | 0.083 | 0.003 | 1.08 | 4.3E−02 | 1.04 | 4.4E−01 | 0.96 | 4.1E−01 |
| PtdEtn 16:0/24:1 | 800.6/255.2 | 0.042 | 0.001 | 0.045 | 0.001 | 0.046 | 0.002 | 1.05 | 1.3E−01 | 1.09 | 6.9E−02 | 1.03 | 5.1E−01 |
| PtdEtn 16:0/26:1 | 828.6/255.2 | 0.024 | 0.001 | 0.024 | 0.001 | 0.026 | 0.001 | 1.01 | 8.2E−01 | 1.08 | 1.9E−01 | 1.07 | 2.1E−01 |
| PtdEtn 16:0/28:1 | 856.7/255.2 | 0.015 | 0.001 | 0.017 | 0.001 | 0.021 | 0.003 | 1.09 | 3.0E−01 | 1.41 | 7.8E−03 | 1.30 | 4.0E−02 |
| PtdEtn 16:0/30:1 | 884.7/255.2 | 0.004 | 0.000 | 0.004 | 0.000 | 0.005 | 0.000 | 0.93 | 4.4E−01 | 1.12 | 3.8E−01 | 1.21 | 9.4E−02 |
| PtdEtn 16:0/32:1 | 912.7/255.2 | 0.003 | 0.000 | 0.004 | 0.000 | 0.004 | 0.000 | 1.15 | 9.0E−02 | 1.14 | 2.7E−01 | 0.99 | 9.6E−01 |
| PtdEtn 16:0/34:1 | 940.8//255.2 | 0.005 | 0.000 | 0.005 | 0.000 | 0.006 | 0.000 | 0.92 | 1.4E−01 | 1.09 | 2.1E−01 | 1.19 | 2.4E−02 |
| PtdEtn 16:0/36:1 | 968.8/255.2 | 0.005 | 0.000 | 0.005 | 0.000 | 0.007 | 0.001 | 0.91 | 1.7E−01 | 1.26 | 9.2E−03 | 1.38 | 4.1E−04 |
| PtdEtn 16:0/38:1 | 996.8/255.2 | 0.003 | 0.000 | 0.003 | 0.000 | 0.004 | 0.000 | 0.94 | 5.5E−01 | 1.17 | 2.8E−01 | 1.25 | 1.1E−01 |
| PtdEtn 16:0/40:1 | 1024.9/255.2 | 0.005 | 0.000 | 0.006 | 0.000 | 0.007 | 0.001 | 1.09 | 2.5E−01 | 1.29 | 4.5E−02 | 1.19 | 1.5E−01 |
| PtdEtn 18:0/18:1 | 744.6/283.2 | 0.359 | 0.031 | 0.284 | 0.024 | 0.645 | 0.145 | 0.79 | 6.0E−02 | 1.80 | 8.1E−03 | 2.28 | 4.2E−04 |
| PtdEtn 18:0/20:1 | 772.6/283.2 | 2.026 | 0.070 | 2.118 | 0.047 | 2.445 | 0.212 | 1.05 | 2.7E−01 | 1.21 | 1.9E−02 | 1.15 | 3.2E−02 |
| PtdEtn 18:0/22:1 | 800.6/283.2 | 0.044 | 0.002 | 0.056 | 0.003 | 0.051 | 0.003 | 1.29 | 1.9E−04 | 1.17 | 3.5E−02 | 0.90 | 2.5E−01 |
| PtdEtn 18:0/24:1 | 828.6/283.2 | 0.023 | 0.001 | 0.028 | 0.001 | 0.026 | 0.002 | 1.24 | 4.8E−04 | 1.16 | 4.1E−02 | 0.93 | 4.1E−01 |
| PtdEtn 18:0/26:1 | 856.7/283.2 | 0.015 | 0.001 | 0.020 | 0.001 | 0.017 | 0.001 | 1.34 | 1.9E−04 | 1.14 | 6.4E−02 | 0.85 | 1.3E−01 |
| PtdEtn 18:0/28:1 | 884.7/283.2 | 0.008 | 0.000 | 0.011 | 0.001 | 0.010 | 0.001 | 1.45 | 1.6E−05 | 1.27 | 5.7E−02 | 0.87 | 3.1E−01 |
| PtdEtn 18:0/30:1 | 912.7/283.2 | 0.002 | 0.000 | 0.003 | 0.000 | 0.002 | 0.000 | 1.32 | 2.8E−02 | 1.26 | 1.8E−01 | 0.95 | 7.6E−01 |
| PtdEtn 18:0/32:1 | 940.8/283.2 | 0.003 | 0.000 | 0.003 | 0.000 | 0.003 | 0.000 | 1.02 | 8.6E−01 | 1.26 | 8.6E−02 | 1.24 | 8.6E−02 |
| PtdEtn 18:0/34:1 | 968.8/283.2 | 0.002 | 0.000 | 0.002 | 0.000 | 0.002 | 0.000 | 1.02 | 8.7E−01 | 1.06 | 7.2E−01 | 1.04 | 7.7E−01 |
| PtdEtn 18:0/36:1 | 996.8/283.2 | 0.002 | 0.000 | 0.003 | 0.000 | 0.003 | 0.000 | 1.04 | 7.0E−01 | 1.11 | 4.9E−01 | 1.07 | 6.4E−01 |
| PtdEtn 18:0/38:1 | 1024.9/283.2 | 0.002 | 0.000 | 0.002 | 0.000 | 0.003 | 0.000 | 1.20 | 2.5E−01 | 1.31 | 1.9E−01 | 1.10 | 6.3E−01 |
| PtdEtn 18:0/40:1 | 1052.9/283.2 | 0.002 | 0.000 | 0.003 | 0.000 | 0.003 | 0.000 | 1.22 | 8.3E−02 | 1.40 | 2.1E−02 | 1.15 | 3.5E−01 |

TABLE 13

Plasma levels of phosphatidylethanolamine (PtdEtn) metabolites with sn-2 position fatty acids containing two unsaturations in non-autistic children, autistic children not taking carnitine supplements, and autistic children taking carnitine supplements (All values are expressed as the ratio to PtdEtn 16:0/18:0).

| Metabolite Name | MS/MS Transition | Control | | Autism | | | | Autism vs. Control | | | | +Carn vs. −Carn | |
|---|---|---|---|---|---|---|---|---|---|---|---|---|---|
| | | | | −Carnitine | | +Carnitine | | −Carnitine | | +Carnitine | | | |
| | | Avg | SEM | Avg | SEM | Avg | SEM | Ratio | p | Ratio | p | Ratio | p |
| PtdEtn 16:0/18:2 | 714.5/255.2 | 0.612 | 0.041 | 0.523 | 0.042 | 0.913 | 0.145 | 0.85 | 1.4E−01 | 1.49 | 9.9E−03 | 1.75 | 1.1E−03 |
| PtdEtn 16:0/20:2 | 742.5/255.2 | 10.816 | 0.270 | 10.963 | 0.487 | 10.679 | 0.654 | 1.01 | 8.0E−01 | 0.99 | 8.2E−01 | 0.97 | 7.5E−01 |
| PtdEtn 16:0/22:2 | 770.6/255.2 | 0.355 | 0.013 | 0.324 | 0.015 | 0.398 | 0.028 | 0.91 | 1.2E−01 | 1.12 | 1.1E−01 | 1.23 | 1.7E−02 |
| PtdEtn 16:0/24:2 | 798.6/255.2 | 0.022 | 0.001 | 0.022 | 0.001 | 0.026 | 0.002 | 1.00 | 9.7E−01 | 1.22 | 9.1E−03 | 1.22 | 9.1E−03 |
| PtdEtn 16:0/26:2 | 826.6/255.2 | 0.041 | 0.002 | 0.040 | 0.002 | 0.041 | 0.002 | 0.98 | 7.3E−01 | 0.98 | 8.5E−01 | 1.01 | 9.5E−01 |
| PtdEtn 16:0/28:2 | 854.7/255.2 | 0.015 | 0.001 | 0.015 | 0.001 | 0.019 | 0.002 | 1.02 | 8.0E−01 | 1.25 | 2.6E−02 | 1.23 | 6.3E−02 |
| PtdEtn 16:0/30:2 | 882.7/255.2 | 0.003 | 0.000 | 0.003 | 0.000 | 0.004 | 0.000 | 0.93 | 4.8E−01 | 1.37 | 3.1E−03 | 1.47 | 2.8E−03 |
| PtdEtn 16:0/32:2 | 910.7/255.2 | 0.003 | 0.000 | 0.003 | 0.000 | 0.004 | 0.001 | 1.07 | 5.5E−01 | 1.32 | 8.9E−02 | 1.24 | 1.6E−01 |
| PtdEtn 16:0/34:2 | 938.8/255.2 | 0.005 | 0.000 | 0.004 | 0.000 | 0.006 | 0.000 | 0.97 | 6.0E−01 | 1.24 | 1.6E−02 | 1.28 | 9.8E−03 |
| PtdEtn 16:0/36:2 | 966.8/255.2 | 0.005 | 0.000 | 0.005 | 0.000 | 0.006 | 0.000 | 1.10 | 2.1E−01 | 1.23 | 5.7E−02 | 1.12 | 2.2E−01 |
| PtdEtn 16:0/38:2 | 994.8/255.2 | 0.003 | 0.000 | 0.003 | 0.000 | 0.004 | 0.001 | 0.89 | 2.8E−01 | 1.27 | 9.2E−02 | 1.42 | 2.7E−02 |
| PtdEtn 16:0/40:2 | 1022.9/255.2 | 0.004 | 0.000 | 0.006 | 0.000 | 0.005 | 0.001 | 1.24 | 8.1E−03 | 1.19 | 7.0E−02 | 0.96 | 7.3E−01 |
| PtdEtn 18:0/18:2 | 742.5/283.2 | 1.216 | 0.092 | 1.092 | 0.098 | 1.977 | 0.430 | 0.90 | 3.6E−01 | 1.62 | 1.7E−02 | 1.81 | 5.4E−03 |
| PtdEtn 18:0/20:2 | 770.6/283.2 | 6.861 | 0.210 | 7.107 | 0.257 | 7.237 | 0.609 | 1.04 | 4.7E−01 | 1.05 | 4.6E−01 | 1.02 | 8.2E−01 |
| PtdEtn 18:0/22:2 | 798.6/283.2 | 0.203 | 0.008 | 0.193 | 0.009 | 0.267 | 0.028 | 0.95 | 3.8E−01 | 1.31 | 4.8E−03 | 1.39 | 1.7E−03 |
| PtdEtn 18:0/24:2 | 826.6/283.2 | 0.012 | 0.001 | 0.013 | 0.001 | 0.016 | 0.002 | 1.04 | 6.3E−01 | 1.30 | 1.7E−02 | 1.26 | 1.9E−02 |
| PtdEtn 18:0/26:2 | 854.7/283.2 | 0.021 | 0.001 | 0.023 | 0.001 | 0.023 | 0.002 | 1.08 | 2.4E−01 | 1.10 | 3.4E−01 | 1.01 | 8.9E−01 |
| PtdEtn 18:0/28:2 | 882.7/283.2 | 0.006 | 0.000 | 0.008 | 0.000 | 0.008 | 0.001 | 1.21 | 9.5E−03 | 1.27 | 3.7E−02 | 1.05 | 6.6E−01 |
| PtdEtn 18:0/30:2 | 910.7/283.2 | 0.002 | 0.000 | 0.003 | 0.000 | 0.003 | 0.000 | 1.42 | 3.2E−03 | 1.50 | 2.1E−02 | 1.05 | 7.4E−01 |
| PtdEtn 18:0/32:2 | 938.8/283.2 | 0.002 | 0.000 | 0.002 | 0.000 | 0.002 | 0.000 | 1.24 | 1.5E−01 | 1.07 | 7.4E−01 | 0.87 | 4.2E−01 |
| PtdEtn 18:0/34:2 | 966.8/283.2 | 0.002 | 0.000 | 0.002 | 0.000 | 0.003 | 0.000 | 1.13 | 3.0E−01 | 1.45 | 2.6E−02 | 1.28 | 1.3E−01 |
| PtdEtn 18:0/36:2 | 994.8/283.2 | 0.002 | 0.000 | 0.002 | 0.000 | 0.002 | 0.000 | 1.17 | 2.3E−01 | 1.19 | 3.4E−01 | 1.02 | 9.1E−01 |
| PtdEtn 18:0/38:2 | 1022.9/283.2 | 0.001 | 0.000 | 0.002 | 0.000 | 0.003 | 0.000 | 1.17 | 2.1E−01 | 1.72 | 2.3E−03 | 1.47 | 2.4E−02 |
| PtdEtn 18:0/40:2 | 1050.9/283.2 | 0.001 | 0.000 | 0.002 | 0.000 | 0.002 | 0.001 | 1.30 | 3.6E−01 | 1.42 | 3.7E−01 | 1.09 | 8.1E−01 |

TABLE 14

Plasma levels of phosphatidylethanolamine (PtdEtn) metabolites with sn-2 position fatty acids containing three unsaturations in non-autistic children, autistic children not taking carnitine supplements, and autistic children taking carnitine supplements (All values are expressed as the ratio to PtdEtn 16:0/18:0).

| Metabolite Name | MS/MS Transition | Control | | Autism | | | | Autism vs. Control | | | | +Carn vs. −Carn | |
|---|---|---|---|---|---|---|---|---|---|---|---|---|---|
| | | | | −Carnitine | | +Carnitine | | −Carnitine | | +Carnitine | | | |
| | | Avg | SEM | Avg | SEM | Avg | SEM | Ratio | p | Ratio | p | Ratio | p |
| PtdEtn 16:0/18:3 | 712.5/255.2 | 0.339 | 0.015 | 0.290 | 0.015 | 0.348 | 0.024 | 0.86 | 2.6E−02 | 1.03 | 7.4E−01 | 1.20 | 5.1E−02 |
| PtdEtn 16:0/20:3 | 740.5/255.2 | 0.309 | 0.015 | 0.251 | 0.010 | 0.339 | 0.039 | 0.81 | 2.1E−03 | 1.10 | 3.7E−01 | 1.35 | 3.5E−03 |
| PtdEtn 16:0/22:3 | 768.6/255.2 | 2.327 | 0.099 | 1.986 | 0.101 | 2.506 | 0.166 | 0.85 | 1.9E−02 | 1.08 | 3.5E−01 | 1.26 | 1.1E−02 |
| PtdEtn 16:0/24:3 | 796.6/255.2 | 0.050 | 0.002 | 0.043 | 0.002 | 0.064 | 0.003 | 0.85 | 1.6E−02 | 1.28 | 1.4E−03 | 1.51 | 5.0E−06 |
| PtdEtn 16:0/26:3 | 824.6/255.2 | 0.023 | 0.001 | 0.030 | 0.004 | 0.031 | 0.005 | 1.33 | 1.1E−01 | 1.37 | 2.7E−02 | 1.03 | 9.1E−01 |
| PtdEtn 16:0/28:3 | 852.6/255.2 | 0.009 | 0.000 | 0.009 | 0.001 | 0.013 | 0.002 | 1.05 | 6.3E−01 | 1.39 | 9.5E−03 | 1.33 | 4.4E−02 |
| PtdEtn 16:0/30:3 | 880.7/255.2 | 0.009 | 0.000 | 0.010 | 0.001 | 0.013 | 0.002 | 1.14 | 3.5E−01 | 1.41 | 1.4E−02 | 1.24 | 3.0E−01 |
| PtdEtn 16:0/32:3 | 908.7/255.2 | 0.004 | 0.000 | 0.004 | 0.000 | 0.005 | 0.001 | 1.18 | 5.3E−02 | 1.41 | 5.5E−03 | 1.19 | 1.5E−01 |
| PtdEtn 16:0/34:3 | 936.7/255.2 | 0.003 | 0.000 | 0.004 | 0.000 | 0.005 | 0.000 | 1.14 | 2.0E−01 | 1.38 | 7.5E−03 | 1.21 | 1.4E−01 |
| PtdEtn 16:0/36:3 | 964.8/255.2 | 0.006 | 0.000 | 0.006 | 0.000 | 0.006 | 0.000 | 1.13 | 7.9E−01 | 1.16 | 1.4E−01 | 1.03 | 7.3E−01 |
| PtdEtn 16:0/38:3 | 992.8/255.2 | 0.005 | 0.000 | 0.005 | 0.000 | 0.006 | 0.001 | 0.89 | 1.6E−01 | 1.15 | 2.1E−01 | 1.29 | 1.1E−02 |
| PtdEtn 16:0/40:3 | 1020.8/255.2 | 0.005 | 0.000 | 0.005 | 0.000 | 0.005 | 0.001 | 1.21 | 4.0E−02 | 1.19 | 2.3E−01 | 0.99 | 9.4E−01 |
| PtdEtn 18:0/18:3 | 740.5/283.2 | 0.185 | 0.008 | 0.169 | 0.009 | 0.218 | 0.019 | 0.91 | 1.6E−01 | 1.17 | 7.0E−02 | 1.29 | 1.2E−02 |
| PtdEtn 18:0/20:3 | 768.6/283.2 | 0.348 | 0.020 | 0.298 | 0.018 | 0.435 | 0.039 | 0.86 | 6.4E−01 | 1.25 | 9.6E−02 | 1.46 | 7.7E−03 |
| PtdEtn 18:0/22:3 | 796.6/283.2 | 1.574 | 0.071 | 1.461 | 0.074 | 1.854 | 0.129 | 0.93 | 2.8E−01 | 1.18 | 5.1E−02 | 1.27 | 1.0E−02 |
| PtdEtn 18:0/24:3 | 824.6/283.2 | 0.029 | 0.002 | 0.026 | 0.001 | 0.042 | 0.003 | 0.87 | 7.2E−02 | 1.44 | 2.3E−04 | 1.65 | 6.9E−07 |
| PtdEtn 18:0/26:3 | 852.6/283.2 | 0.012 | 0.001 | 0.014 | 0.003 | 0.013 | 0.002 | 1.20 | 4.9E−01 | 1.10 | 5.7E−01 | 0.92 | 8.3E−01 |
| PtdEtn 18:0/28:3 | 880.7/283.2 | 0.006 | 0.000 | 0.006 | 0.000 | 0.006 | 0.001 | 1.01 | 9.6E−01 | 1.10 | 3.9E−01 | 1.10 | 4.7E−01 |
| PtdEtn 18:0/30:3 | 908.7/283.2 | 0.004 | 0.000 | 0.005 | 0.000 | 0.006 | 0.001 | 1.15 | 2.2E−01 | 1.43 | 1.4E−02 | 1.24 | 1.8E−01 |
| PtdEtn 18:0/32:3 | 936.7/283.2 | 0.002 | 0.000 | 0.002 | 0.000 | 0.001 | 0.000 | 1.12 | 3.3E−01 | 0.77 | 1.3E−01 | 0.69 | 3.8E−02 |
| PtdEtn 18:0/34:3 | 964.8/283.2 | 0.002 | 0.000 | 0.002 | 0.000 | 0.003 | 0.001 | 1.13 | 5.5E−01 | 1.61 | 1.1E−01 | 1.43 | 1.7E−01 |
| PtdEtn 18:0/36:3 | 992.8/283.2 | 0.003 | 0.000 | 0.003 | 0.000 | 0.004 | 0.001 | 0.95 | 7.0E−01 | 1.32 | 2.1E−01 | 1.38 | 9.4E−02 |
| PtdEtn 18:0/38:3 | 1020.8/283.2 | 0.002 | 0.000 | 0.002 | 0.000 | 0.002 | 0.000 | 1.10 | 5.2E−01 | 1.30 | 1.4E−01 | 1.18 | 3.1E−01 |
| PtdEtn 18:0/40:3 | 1048.9/283.2 | 0.002 | 0.000 | 0.002 | 0.000 | 0.004 | 0.001 | 1.08 | 5.9E−01 | 1.80 | 2.3E−02 | 1.67 | 3.0E−02 |

TABLE 15

Plasma levels of phosphatidylethanolamine (PtdEtn) metabolites with sn-2 position fatty acids containing four unsaturations in non-autistic children, autistic children not taking carnitine supplements, and autistic children taking carnitine supplements (All values are expressed as the ratio to PtdEtn 16:0/18:0).

| Metabolite Name | MS/MS Transition | Control | | Autism −Carnitine | | Autism +Carnitine | | Autism vs. Control −Carnitine | | Autism vs. Control +Carnitine | | +Carn vs. −Carn | |
|---|---|---|---|---|---|---|---|---|---|---|---|---|---|
| | | Avg | SEM | Avg | SEM | Avg | SEM | Ratio | p | Ratio | p | Ratio | p |
| PtdEtn 16:0/20:4 | 738.5/255.2 | 0.541 | 0.036 | 0.479 | 0.032 | 0.900 | 0.099 | 0.88 | 2.0E−01 | 1.66 | 1.2E−04 | 1.88 | 4.1E−06 |
| PtdEtn 16:0/22:4 | 766.5/255.2 | 4.431 | 0.197 | 4.206 | 0.187 | 4.811 | 0.268 | 0.95 | 4.1E−01 | 1.09 | 2.9E−01 | 1.14 | 9.2E−02 |
| PtdEtn 16:0/24:4 | 794.6/255.2 | 0.309 | 0.013 | 0.285 | 0.016 | 0.389 | 0.024 | 0.92 | 2.5E−01 | 1.26 | 4.0E−03 | 1.36 | 1.5E−03 |
| PtdEtn 16:0/26:4 | 822.6/255.2 | 0.012 | 0.001 | 0.013 | 0.000 | 0.014 | 0.001 | 1.09 | 1.4E−01 | 1.21 | 4.1E−02 | 1.11 | 1.5E−01 |
| PtdEtn 16:0/28:4 | 850.6/255.2 | 0.015 | 0.001 | 0.014 | 0.001 | 0.018 | 0.002 | 0.94 | 3.8E−01 | 1.19 | 6.6E−02 | 1.26 | 1.0E−02 |
| PtdEtn 16:0/30:4 | 878.7/255.2 | 0.017 | 0.001 | 0.017 | 0.001 | 0.019 | 0.001 | 1.00 | 9.7E−01 | 1.13 | 1.0E−01 | 1.13 | 2.2E−01 |
| PtdEtn 16:0/32:4 | 906.7/255.2 | 0.010 | 0.000 | 0.011 | 0.000 | 0.012 | 0.001 | 1.10 | 6.7E−02 | 1.28 | 1.3E−03 | 1.16 | 6.1E−02 |
| PtdEtn 16:0/34:4 | 934.7/255.2 | 0.003 | 0.000 | 0.003 | 0.000 | 0.004 | 0.000 | 1.19 | 1.4E−01 | 1.52 | 2.9E−03 | 1.28 | 6.4E−02 |
| PtdEtn 16:0/36:4 | 962.8/255.2 | 0.005 | 0.000 | 0.005 | 0.000 | 0.005 | 0.000 | 1.07 | 3.4E−01 | 1.03 | 7.8E−01 | 0.96 | 6.8E−01 |
| PtdEtn 16:0/38:4 | 990.8/255.2 | 0.006 | 0.000 | 0.006 | 0.000 | 0.007 | 0.001 | 1.06 | 3.5E−01 | 1.20 | 1.5E−02 | 1.13 | 1.8E−01 |
| PtdEtn 16:0/40:4 | 1018.8/255.2 | 0.002 | 0.000 | 0.003 | 0.000 | 0.003 | 0.000 | 1.07 | 5.1E−01 | 1.40 | 1.7E−02 | 1.31 | 6.0E−02 |
| PtdEtn 18:0/20:4 | 766.5/283.2 | 1.420 | 0.095 | 1.419 | 0.106 | 2.433 | 0.273 | 1.00 | 1.0E+00 | 1.71 | 6.6E−05 | 1.71 | 1.2E−04 |
| PtdEtn 18:0/22:4 | 794.6/283.2 | 3.068 | 0.137 | 3.231 | 0.185 | 3.686 | 0.261 | 1.05 | 4.9E−01 | 1.20 | 2.8E−02 | 1.14 | 1.9E−01 |
| PtdEtn 18:0/24:4 | 822.6/283.2 | 0.141 | 0.006 | 0.134 | 0.008 | 0.203 | 0.014 | 0.95 | 5.1E−01 | 1.44 | 2.9E−05 | 1.51 | 7.4E−05 |
| PtdEtn 18:0/26:4 | 850.6/283.2 | 0.007 | 0.000 | 0.008 | 0.000 | 0.010 | 0.001 | 1.06 | 4.1E−01 | 1.36 | 8.4E−04 | 1.29 | 1.3E−03 |
| PtdEtn 18:0/28:4 | 878.7/283.2 | 0.012 | 0.001 | 0.012 | 0.001 | 0.017 | 0.001 | 1.01 | 9.2E−01 | 1.40 | 4.0E−04 | 1.38 | 3.7E−03 |
| PtdEtn 18:0/30:4 | 906.7/283.2 | 0.008 | 0.000 | 0.009 | 0.000 | 0.010 | 0.001 | 1.15 | 5.3E−02 | 1.23 | 1.6E−02 | 1.07 | 4.9E−01 |
| PtdEtn 18:0/32:4 | 934.7/283.2 | 0.002 | 0.000 | 0.002 | 0.000 | 0.003 | 0.000 | 0.99 | 9.6E−01 | 1.30 | 1.1E−01 | 1.31 | 6.9E−02 |
| PtdEtn 18:0/34:4 | 962.8/283.2 | 0.003 | 0.000 | 0.003 | 0.000 | 0.003 | 0.000 | 1.04 | 7.4E−01 | 1.22 | 1.9E−01 | 1.17 | 2.4E−01 |
| PtdEtn 18:0/36:4 | 990.8/283.2 | 0.002 | 0.000 | 0.002 | 0.000 | 0.003 | 0.000 | 0.96 | 8.6E−01 | 1.53 | 5.8E−02 | 1.59 | 6.0E−02 |
| PtdEtn 18:0/38:4 | 1018.8/283.2 | 0.002 | 0.000 | 0.002 | 0.000 | 0.003 | 0.000 | 1.08 | 4.5E−01 | 1.32 | 4.2E−02 | 1.22 | 1.8E−01 |
| PtdEtn 18:0/40:4 | 1046.9/283.2 | 0.002 | 0.000 | 0.002 | 0.000 | 0.003 | 0.001 | 1.25 | 1.1E−01 | 1.43 | 6.6E−02 | 1.14 | 5.0E−01 |

TABLE 16

Plasma levels of phosphatidylethanolamine (PtdEtn) metabolites with sn-2 position fatty acids containing five unsaturations in non-autistic children, autistic children not taking carnitine supplements, and autistic children taking carnitine supplements (All values are expressed as the ratio to PtdEtn 16:0/18:0).

| Metabolite Name | MS/MS Transition | Control | | Autism −Carnitine | | Autism +Carnitine | | Autism vs. Control −Carnitine | | Autism vs. Control +Carnitine | | +Carn vs. −Carn | |
|---|---|---|---|---|---|---|---|---|---|---|---|---|---|
| | | Avg | SEM | Avg | SEM | Avg | SEM | Ratio | p | Ratio | p | Ratio | p |
| PtdEtn 16:0/20:5 | 736.5/255.2 | 0.118 | 0.005 | 0.131 | 0.010 | 0.137 | 0.010 | 1.11 | 3.0E−01 | 1.15 | 9.8E−02 | 1.04 | 7.6E−01 |
| PtdEtn 16:0/22:5 | 764.5/255.2 | 0.450 | 0.030 | 0.616 | 0.118 | 0.505 | 0.049 | 1.37 | 1.9E−01 | 1.12 | 3.3E−01 | 0.82 | 5.8E−01 |
| PtdEtn 16:0/24:5 | 792.6/255.2 | 0.774 | 0.031 | 0.907 | 0.048 | 0.825 | 0.079 | 1.17 | 2.6E−02 | 1.07 | 4.6E−01 | 0.91 | 3.8E−01 |
| PtdEtn 16:0/26:5 | 820.6/255.2 | 0.028 | 0.001 | 0.030 | 0.001 | 0.032 | 0.003 | 1.08 | 9.8E−01 | 1.14 | 1.3E−01 | 1.05 | 5.1E−01 |
| PtdEtn 16:0/28:5 | 848.6/255.2 | 0.015 | 0.001 | 0.016 | 0.001 | 0.018 | 0.001 | 1.04 | 6.1E−01 | 1.20 | 9.0E−02 | 1.15 | 1.0E−01 |
| PtdEtn 16:0/30:5 | 876.6/255.2 | 0.009 | 0.000 | 0.009 | 0.000 | 0.012 | 0.001 | 1.06 | 4.1E−01 | 1.35 | 1.0E−02 | 1.27 | 1.3E−02 |
| PtdEtn 16:0/32:5 | 904.7/255.2 | 0.014 | 0.001 | 0.015 | 0.001 | 0.018 | 0.001 | 1.04 | 6.2E−01 | 1.31 | 1.4E−02 | 1.26 | 2.3E−02 |
| PtdEtn 16:0/34:5 | 932.7/255.2 | 0.010 | 0.001 | 0.009 | 0.000 | 0.011 | 0.001 | 0.96 | 5.6E−01 | 1.18 | 1.1E−01 | 1.23 | 1.7E−02 |
| PtdEtn 16:0/36:5 | 960.7/255.2 | 0.002 | 0.000 | 0.003 | 0.000 | 0.002 | 0.000 | 1.07 | 5.7E−01 | 1.06 | 7.7E−01 | 0.98 | 9.2E−01 |
| PtdEtn 16:0/38:5 | 988.8/255.2 | 0.005 | 0.000 | 0.005 | 0.000 | 0.005 | 0.000 | 1.07 | 4.3E−01 | 1.02 | 8.4E−01 | 0.96 | 6.9E−01 |
| PtdEtn 16:0/40:5 | 1016.8/255.2 | 0.003 | 0.000 | 0.003 | 0.000 | 0.004 | 0.000 | 1.10 | 2.9E−01 | 1.19 | 1.7E−01 | 1.08 | 4.2E−01 |
| PtdEtn 18:0/20:5 | 764.5/283.2 | 0.098 | 0.007 | 0.136 | 0.024 | 0.140 | 0.018 | 1.39 | 1.4E−01 | 1.43 | 1.1E−02 | 1.03 | 9.3E−01 |
| PtdEtn 18:0/22:5 | 792.6/283.2 | 0.356 | 0.023 | 0.555 | 0.101 | 0.437 | 0.043 | 1.56 | 7.1E−02 | 1.23 | 7.9E−02 | 0.79 | 4.9E−01 |
| PtdEtn 18:0/24:5 | 820.6/283.2 | 0.304 | 0.012 | 0.390 | 0.025 | 0.384 | 0.032 | 1.28 | 3.5E−03 | 1.26 | 5.8E−03 | 0.98 | 8.9E−01 |
| PtdEtn 18:0/26:5 | 848.6/283.2 | 0.018 | 0.001 | 0.019 | 0.001 | 0.022 | 0.002 | 1.07 | 1.9E−01 | 1.21 | 9.4E−03 | 1.13 | 1.2E−01 |
| PtdEtn 18:0/28:5 | 876.6/283.2 | 0.008 | 0.001 | 0.008 | 0.001 | 0.009 | 0.001 | 0.99 | 9.3E−01 | 1.12 | 5.0E−01 | 1.13 | 4.8E−01 |
| PtdEtn 18:0/30:5 | 904.7/283.2 | 0.005 | 0.000 | 0.005 | 0.000 | 0.006 | 0.001 | 1.10 | 3.1E−01 | 1.41 | 3.4E−02 | 1.28 | 6.5E−02 |
| PtdEtn 18:0/32:5 | 932.7/283.2 | 0.008 | 0.001 | 0.008 | 0.000 | 0.010 | 0.001 | 1.01 | 9.2E−01 | 1.35 | 3.1E−02 | 1.34 | 1.6E−02 |
| PtdEtn 18:0/34:5 | 960.7/283.2 | 0.004 | 0.000 | 0.004 | 0.000 | 0.005 | 0.001 | 1.03 | 7.0E−01 | 1.34 | 2.4E−02 | 1.29 | 2.1E−02 |
| PtdEtn 18:0/36:5 | 988.8/283.2 | 0.001 | 0.000 | 0.002 | 0.000 | 0.002 | 0.000 | 1.17 | 2.3E−01 | 1.28 | 1.7E−01 | 1.10 | 6.2E−01 |
| PtdEtn 18:0/38:5 | 1016.8/283.2 | 0.002 | 0.000 | 0.003 | 0.000 | 0.003 | 0.000 | 1.26 | 6.2E−02 | 1.24 | 1.1E−01 | 0.99 | 9.3E−01 |
| PtdEtn 18:0/40:5 | 1044.8/283.2 | 0.002 | 0.000 | 0.002 | 0.000 | 0.002 | 0.000 | 1.12 | 2.8E−01 | 1.40 | 1.7E−02 | 1.25 | 5.9E−02 |

TABLE 17

Plasma levels of phosphatidylethanolamine (PtdEtn) metabolites with sn-2 position fatty acids containing six unsaturations in non-autistic children, autistic children not taking carnitine supplements, and autistic children taking carnitine supplements (All values are expressed as the ratio to PtdEtn 16:0/18:0).

| Metabolite Name | MS/MS Transition | Control Avg | Control SEM | Autism −Carnitine Avg | Autism −Carnitine SEM | Autism +Carnitine Avg | Autism +Carnitine SEM | Autism vs. Control −Carnitine Ratio | Autism vs. Control −Carnitine p | Autism vs. Control +Carnitine Ratio | Autism vs. Control +Carnitine p | +Carn vs. −Carn Ratio | +Carn vs. −Carn p |
|---|---|---|---|---|---|---|---|---|---|---|---|---|---|
| PtdEtn 16:0/20:6 | 734.5/255.2 | 0.151 | 0.009 | 0.276 | 0.026 | 0.132 | 0.010 | 1.83 | 4.5E−05 | 0.87 | 2.1E−01 | 0.48 | 1.9E−03 |
| PtdEtn 16:0/22:6 | 762.5/255.2 | 0.351 | 0.033 | 0.532 | 0.052 | 0.363 | 0.034 | 1.52 | 5.7E−03 | 1.04 | 8.3E−01 | 0.68 | 6.6E−02 |
| PtdEtn 16:0/24:6 | 790.5/255.2 | 0.836 | 0.050 | 1.678 | 0.169 | 0.707 | 0.078 | 2.01 | 2.4E−05 | 0.85 | 1.8E−01 | 0.42 | 1.5E−03 |
| PtdEtn 16:0/26:6 | 818.6/255.2 | 0.029 | 0.001 | 0.030 | 0.002 | 0.031 | 0.003 | 1.03 | 7.3E−01 | 1.09 | 4.1E−01 | 1.06 | 6.0E−01 |
| PtdEtn 16:0/28:6 | 846.6/255.2 | 0.009 | 0.000 | 0.010 | 0.000 | 0.011 | 0.001 | 1.12 | 1.1E−01 | 1.22 | 2.8E−02 | 1.09 | 3.1E−01 |
| PtdEtn 16:0/30:6 | 874.6/255.2 | 0.010 | 0.001 | 0.012 | 0.001 | 0.010 | 0.001 | 1.21 | 5.8E−02 | 1.05 | 7.7E−01 | 0.86 | 2.0E−01 |
| PtdEtn 16:0/32:6 | 902.7/255.2 | 0.014 | 0.002 | 0.016 | 0.001 | 0.017 | 0.001 | 1.09 | 4.3E−01 | 1.21 | 2.7E−01 | 1.10 | 2.9E−01 |
| PtdEtn 16:0/34:6 | 930.7/255.2 | 0.007 | 0.000 | 0.008 | 0.000 | 0.010 | 0.000 | 1.11 | 1.6E−01 | 1.30 | 6.8E−03 | 1.17 | 6.1E−02 |
| PtdEtn 16:0/36:6 | 958.7/255.2 | 0.003 | 0.000 | 0.003 | 0.000 | 0.004 | 0.000 | 0.95 | 6.2E−01 | 1.20 | 1.6E−01 | 1.27 | 1.0E−01 |
| PtdEtn 16:0/38:6 | 986.8/255.2 | 0.004 | 0.000 | 0.005 | 0.000 | 0.005 | 0.001 | 1.15 | 9.1E−02 | 1.22 | 1.1E−01 | 1.06 | 5.8E−01 |
| PtdEtn 16:0/40:6 | 1014.8/255.2 | 0.003 | 0.000 | 0.003 | 0.000 | 0.004 | 0.000 | 1.01 | 9.1E−01 | 1.10 | 3.5E−01 | 1.09 | 4.2E−01 |
| PtdEtn 18:0/20:6 | 762.5/283.2 | 0.124 | 0.009 | 0.216 | 0.021 | 0.128 | 0.008 | 1.75 | 2.3E−04 | 1.03 | 7.9E−01 | 0.59 | 1.6E−02 |
| PtdEtn 18:0/22:6 | 790.5/283.2 | 0.392 | 0.030 | 0.728 | 0.079 | 0.410 | 0.036 | 1.86 | 3.3E−04 | 1.05 | 7.3E−01 | 0.56 | 2.3E−02 |
| PtdEtn 18:0/24:6 | 818.6/283.2 | 0.456 | 0.026 | 0.957 | 0.105 | 0.470 | 0.045 | 2.10 | 3.8E−05 | 1.03 | 7.9E−01 | 0.49 | 8.6E−03 |
| PtdEtn 18:0/26:6 | 846.6/283.2 | 0.011 | 0.000 | 0.013 | 0.001 | 0.014 | 0.001 | 1.19 | 2.3E−02 | 1.25 | 5.7E−03 | 1.05 | 6.4E−01 |
| PtdEtn 18:0/28:6 | 874.6/283.2 | 0.005 | 0.000 | 0.007 | 0.000 | 0.006 | 0.001 | 1.28 | 9.0E−03 | 1.17 | 1.7E−01 | 0.91 | 4.5E−01 |
| PtdEtn 18:0/30:6 | 902.7/283.2 | 0.007 | 0.001 | 0.009 | 0.001 | 0.008 | 0.001 | 1.26 | 7.7E−02 | 1.17 | 3.8E−01 | 0.94 | 6.2E−01 |
| PtdEtn 18:0/32:6 | 930.7/283.2 | 0.006 | 0.001 | 0.007 | 0.000 | 0.009 | 0.001 | 1.18 | 9.8E−02 | 1.38 | 2.9E−02 | 1.16 | 1.6E−01 |
| PtdEtn 18:0/34:6 | 958.7/283.2 | 0.003 | 0.000 | 0.004 | 0.000 | 0.005 | 0.000 | 1.22 | 3.1E−02 | 1.42 | 4.4E−03 | 1.17 | 1.4E−01 |
| PtdEtn 18:0/36:6 | 986.8/283.2 | 0.002 | 0.000 | 0.003 | 0.000 | 0.003 | 0.000 | 1.28 | 7.1E−02 | 1.62 | 2.5E−03 | 1.26 | 1.3E−01 |
| PtdEtn 18:0/38:6 | 1014.8/283.2 | 0.002 | 0.000 | 0.003 | 0.000 | 0.002 | 0.000 | 1.07 | 5.7E−01 | 0.98 | 9.0E−01 | 0.92 | 5.8E−01 |
| PtdEtn 18:0/40:6 | 1042.8/283.2 | 0.001 | 0.000 | 0.002 | 0.000 | 0.003 | 0.001 | 1.20 | 3.4E−01 | 1.79 | 2.7E−02 | 1.49 | 1.0E−01 |

TABLE 18

Plasma levels of ethanolamine plasmalogens (PlsEtn) metabolites with selected sn-2 position fatty acids in non-autistic children, autistic children not taking carnitine supplements, and autistic children taking carnitine supplements (All values are expressed as the ratio to PtdEtn 16:0/18:0).

| Metabolite Name | MS/MS Transition | Control Avg | Control SEM | Autism −Carnitine Avg | Autism −Carnitine SEM | Autism +Carnitine Avg | Autism +Carnitine SEM | Autism vs. Control −Carnitine Ratio | Autism vs. Control −Carnitine p | Autism vs. Control +Carnitine p | +Carn vs. −Carn Ratio | +Carn vs. −Carn p |
|---|---|---|---|---|---|---|---|---|---|---|---|---|
| PlsEtn 16:0/18:1 | 700.5/281.2 | 0.626 | 0.027 | 0.669 | 0.025 | 0.727 | 0.067 | 1.07 | 2.5E−01 | 9.7E−02 | 1.09 | 3.3E−01 |
| PlsEtn 16:0/18:2 | 698.5/279.2 | 1.987 | 0.096 | 2.206 | 0.109 | 2.333 | 0.309 | 1.11 | 1.4E−01 | 1.6E−01 | 1.06 | 6.2E−01 |
| PlsEtn 16:0/18:3 | 696.5/277.2 | 0.033 | 0.002 | 0.032 | 0.002 | 0.039 | 0.005 | 0.98 | 7.9E−01 | 2.1E−01 | 1.21 | 1.1E−01 |
| PlsEtn 16:0/20:4 | 722.5/303.2 | 3.289 | 0.218 | 4.096 | 0.306 | 3.969 | 0.622 | 1.25 | 3.9E−02 | 2.0E−01 | 0.97 | 8.4E−01 |
| PlsEtn 16:0/22:6 | 746.5/327.2 | 0.495 | 0.031 | 1.021 | 0.096 | 0.446 | 0.049 | 2.06 | 5.2E−06 | 4.0E−01 | 0.44 | 1.0E−03 |
| PlsEtn 18:0/18:1 | 728.5/281.2 | 0.782 | 0.034 | 0.925 | 0.047 | 0.902 | 0.078 | 1.18 | 1.8E−02 | 1.0E−01 | 0.98 | 8.1E−01 |
| PlsEtn 18:0/18:2 | 726.5/279.2 | 3.010 | 0.167 | 3.284 | 0.172 | 3.058 | 0.340 | 1.09 | 2.6E−01 | 8.9E−01 | 0.93 | 5.2E−01 |
| PlsEtn 18:0/18:3 | 724.5/277.2 | 0.046 | 0.003 | 0.047 | 0.003 | 0.052 | 0.008 | 1.02 | 8.2E−01 | 4.1E−01 | 1.11 | 4.3E−01 |
| PlsEtn 18:0/20:4 | 750.5/303.2 | 6.899 | 0.412 | 8.803 | 0.721 | 8.025 | 1.056 | 1.28 | 2.9E−02 | 2.3E−01 | 0.91 | 5.7E−01 |
| PlsEtn 18:0/22:6 | 774.5/327.2 | 0.669 | 0.039 | 1.406 | 0.141 | 0.628 | 0.062 | 2.10 | 1.0E−05 | 5.8E−01 | 0.45 | 2.2E−03 |
| PlsEtn 18:1/18:1 | 726.5/281.2 | 0.520 | 0.031 | 0.629 | 0.029 | 0.628 | 0.065 | 1.21 | 1.2E−02 | 1.0E−01 | 1.00 | 9.8E−01 |
| PlsEtn 18:1/18:2 | 724.5/279.2 | 1.402 | 0.100 | 1.573 | 0.085 | 1.664 | 0.280 | 1.12 | 1.9E−01 | 2.7E−01 | 1.06 | 6.8E−01 |
| PlsEtn 18:1/18:3 | 722.5/277.2 | 0.023 | 0.002 | 0.025 | 0.001 | 0.030 | 0.004 | 1.06 | 5.9E−01 | 1.8E−01 | 1.19 | 1.6E−01 |
| PlsEtn 18:1/20:4 | 748.5/303.2 | 3.425 | 0.230 | 4.177 | 0.292 | 4.083 | 0.489 | 1.22 | 5.0E−02 | 1.7E−01 | 0.98 | 8.7E−01 |
| PlsEtn 18:1/22:6 | 772.5/327.2 | 0.411 | 0.024 | 0.875 | 0.082 | 0.408 | 0.044 | 2.13 | 2.7E−06 | 9.3E−01 | 0.47 | 1.8E−03 |

All references identified herein are incorporated herein by reference.

The present invention has been described with regard to a plurality of illustrative embodiments. However, it will be apparent to persons skilled in the art that a number of variations and modifications can be made without departing from the scope of the invention as defined in the claims.

References

American Psychiatric Association (1994). *Diagnostic and Statistical Manual of Mental Disorders-Fourth Edition.*

Bauman, M. L. and T. L. Kemper (2005). "Neuroanatomic observations of the brain in autism: a review and future directions." *Int J Dev Neurosci* 23(2-3): 183-7.

Chauhan, A. and V. Chauhan (2006). "Oxidative stress in autism." *Pathophysiology* 13(3): 171-81.

Chauhan, A., V. Chauhan, et al. (2004). "Oxidative stress in autism: increased lipid peroxidation and reduced serum levels of ceruloplasmin and transferrin—the antioxidant proteins." *Life Sci* 75(21): 2539-49.

Clark-Taylor, T. and B. E. Clark-Taylor (2004). "Is autism a disorder of fatty acid metabolism? Possible dysfunction of mitochondrial beta-oxidation by long chain acyl-CoA dehydrogenase." *Med Hypotheses* 62(6): 970-5.

Courchesne, E. (1997). "Brainstem, cerebellar and limbic neuroanatomical abnormalities in autism." *Curr Opin Neurobiol* 7(2): 269-78.

Courchesne, E., E. Redcay, et al. (2004). "The autistic brain: birth through adulthood." Curr *Opin Neurol* 17(4): 489-96.

James, S. J., P. Cutler, et al. (2004). "Metabolic biomarkers of increased oxidative stress and impaired methylation capacity in children with autism." *Am J Clin Nutr* 80(6): 1611-7.

Kern, J. K. and A. M. Jones (2006). "Evidence of toxicity, oxidative stress, and neuronal insult in autism." *J Toxicol Environ Health B Crit Rev* 9(6): 485-99.

Lombard, J. (1998). "Autism: a mitochondrial disorder?" *Med Hypotheses* 50(6): 497-500.

Newschaffer, C. J., D. Fallin, et al. (2002) "Heritable and nonheritable risk factors for autism spectrum disorders." *Epidemiol Rev* 24(2): 137-53.

Palmen, S. J., H. van Engeland, et al. (2004). "Neuropathological findings in autism." *Brain* 127(Pt 12): 2572-83.

Pettegrew, J. W., J. Levine, et al. (2000). "Acetyl-L-carnitine physical-chemical, metabolic, and therapeutic properties: relevance for its mode of action in Alzheimer's disease and geriatric depression." *Mol Psychiatry* 5(6): 616-32.

Skuse, D. H. (2000). "Imprinting, the X-chromosome, and the male brain: explaining sex differences in the liability to autism." *Pediatr Res* 47(1): 9-16.

Sogut, S., S. S. Zoroglu, et al. (2003). "Changes in nitric oxide levels and antioxidant enzyme activities may have a role in the pathophysiological mechanisms involved in autism." *Clin Chim Acta* 331(1-2): 111-7.

Yeargin-Allsopp, M., C. Rice, et al. (2003). "Prevalence of autism in a US metropolitan area." *Jama* 289(1): 49-55.

Yorbik, O., A. Sayal, et al. (2002). "Investigation of antioxidant enzymes in children with autistic disorder." *Prostaglandins Leukot Essent Fatty Acids* 67(5): 341-3.

Zoroglu, S. S., F. Armutcu, et al. (2004). "Increased oxidative stress and altered activities of erythrocyte free radical scavenging enzymes in autism." *Eur Arch Psychiatry Clin Neurosci* 254(3): 143-7.

I claim:

1. A method for diagnosing a human subject's Autism Spectrum Disorder (ASD) health state or change in ASD health state or identifying a human subject's risk of ASD, the method comprising the steps of:
    a) analyzing at least one blood sample from said subject using an analytic device or system comprising a mass spectrometer; to obtain quantifying data for one or more than one metabolite marker;
    b) comparing the quantifying data for said one or more than one metabolite marker to corresponding data obtained from one or more than one reference blood sample to identify an increase or decrease in the level of said one or more than one metabolite marker in said blood sample; and
    c) using said increase or decrease in the level of said one or more than one metabolite marker to diagnose the human subject's ASD health state or change in ASD health state, or to identify the risk of ASD in said subject,
    wherein the one or more than one metabolite marker comprises one or more than one molecule selected from the group consisting of: ethanolamine phospholipids; docosahexaenoic acid (DHA)-containing phospholipids; DHA precursor-containing phospholipids; catabolic products of DHA beta-oxidation-containing phospholipids; polyunsaturated very long chain fatty acids (VLCFA) containing phospholipids; and combinations thereof, and
    wherein the human subject is diagnosed with ASD based on having: elevated levels of ethanolamine phospholipids containing saturated or monounsaturated VLCFA, docosahexaenoic acid (22:6, DHA), VLCFA DHA precursor (24:5, 24:6), catabolic products of DHA beta-oxidation (20:6), or polyunsaturated VLCFA; decreased levels of ethanolamine phospholipids containing 18:3, 20:3, 22:3, 24:3 fatty acids; or combinations thereof.

2. The method of claim 1, wherein said method comprises monitoring an ASD therapy in the human subject, and wherein said increase or decrease in the level of said one or more than one metabolite marker is used in step (c) to determine whether the therapy is improving the biochemical state of the subject.

3. The method of claim 2, wherein the therapy is a carnitine therapy.

4. The method of claim 1, wherein the one or more than one metabolite marker is selected from the group consisting of: PtdEtn 16:0/18:0, PtdEtn 16:0/20:0, PtdEtn 16:0/22:0, PtdEtn 16:0/24:0, PtdEtn 16:0/26:0, PtdEtn 16:0/28:0, PtdEtn 16:0/30:0, PtdEtn 16:0/32:0, PtdEtn 16:0/34:0, PtdEtn 16:0/36:0, PtdEtn 16:0/38:0, PtdEtn 16:0/40:0, PtdEtn 18:0/18:0, PtdEtn 18:0/20:0, PtdEtn 18:0/22:0, PtdEtn 18:0/24:0, PtdEtn 18:0/26:0, PtdEtn 18:0/28:0, PtdEtn 18:0/30:0, PtdEtn 18:0/32:0, PtdEtn 18:0/34:0, PtdEtn 18:0/36:0, PtdEtn 18:0/38:0, PtdEtn 18:0/40:0, PtdEtn 16:0/18:1, PtdEtn 16:0/20:1, PtdEtn 16:0/22:1, PtdEtn 16:0/24:1, PtdEtn 16:0/26:1, PtdEtn 16:0/28:1, PtdEtn 16:0/30:1, PtdEtn 16:0/32:1, PtdEtn 16:0/34:1, PtdEtn 16:0/36:1, PtdEtn 16:0/38:1, PtdEtn 16:0/40:1, PtdEtn 18:0/18:1, PtdEtn 18:0/20:1, PtdEtn 18:0/22:1, PtdEtn 18:0/24:1, PtdEtn 18:0/26:1, PtdEtn 18:0/28:1, PtdEtn 18:0/30:1, PtdEtn 18:0/32:1, PtdEtn 18:0/34:1, PtdEtn 18:0/36:1, PtdEtn 18:0/38:1, PtdEtn 18:0/40:1, PtdEtn 16:0/18:2, PtdEtn 16:0/20:2, PtdEtn 16:0/22:2, PtdEtn 16:0/24:2, PtdEtn 16:0/26:2, PtdEtn 16:0/28:2, PtdEtn 16:0/30:2, PtdEtn 16:0/32:2, PtdEtn 16:0/34:2, PtdEtn 16:0/36:2, PtdEtn 16:0/38:2, PtdEtn 16:0/40:2, PtdEtn 18:0/18:2, PtdEtn 18:0/20:2, PtdEtn 18:0/22:2, PtdEtn 18:0/24:2, PtdEtn 18:0/26:2, PtdEtn 18:0/28:2, PtdEtn 18:0/30:2, PtdEtn 18:0/32:2, PtdEtn 18:0/34:2, PtdEtn 18:0/36:2, PtdEtn 18:0/38:2, PtdEtn 18:0/40:2, PtdEtn 16:0/18:3, PtdEtn 16:0/20:3, PtdEtn 16:0/22:3, PtdEtn 16:0/24:3, PtdEtn 16:0/26:3, PtdEtn 16:0/28:3, PtdEtn 16:0/30:3, PtdEtn 16:0/32:3, PtdEtn 16:0/34:3, PtdEtn 16:0/36:3, PtdEtn 16:0/38:3, PtdEtn 16:0/40:3, PtdEtn 18:0/18:3, PtdEtn 18:0/20:3, PtdEtn 18:0/22:3, PtdEtn 18:0/24:3, PtdEtn 18:0/26:3, PtdEtn 18:0/28:3, PtdEtn 18:0/30:3, PtdEtn 18:0/32:3, PtdEtn 18:0/34:3, PtdEtn 18:0/36:3, PtdEtn 18:0/38:3, PtdEtn 18:0/40:3, PtdEtn 16:0/20:4, PtdEtn 16:0/22:4, PtdEtn 16:0/24:4, PtdEtn 16:0/26:4, PtdEtn 16:0/28:4, PtdEtn 16:0/30:4, PtdEtn 16:0/32:4, PtdEtn 16:0/34:4, PtdEtn 16:0/36:4, PtdEtn 16:0/38:4, PtdEtn 16:0/40:4, PtdEtn 18:0/20:4, PtdEtn 18:0/22:4, PtdEtn 18:0/24:4, PtdEtn 18:0/26:4, PtdEtn 18:0/28:4, PtdEtn 18:0/30:4, PtdEtn 18:0/32:4, PtdEtn 18:0/34:4, PtdEtn 18:0/36:4, PtdEtn 18:0/38:4, PtdEtn 18:0/40:4, PtdEtn 16:0/20:5, PtdEtn 16:0/22:5, PtdEtn 16:0/24:5, PtdEtn 16:0/26:5, PtdEtn 16:0/28:5, PtdEtn 16:0/30:5, PtdEtn 16:0/32:5, PtdEtn 16:0/34:5, PtdEtn 16:0/36:5, PtdEtn 16:0/38:5, PtdEtn 16:0/40:5, PtdEtn 18:0/20:5, PtdEtn 18:0/22:5, PtdEtn 18:0/24:5, PtdEtn 18:0/26:5, PtdEtn 18:0/28:5, PtdEtn 18:0/30:5, PtdEtn 18:0/32:5, PtdEtn 18:0/34:5, PtdEtn 18:0/36:5, PtdEtn 18:0/38:5, PtdEtn 18:0/40:5, PtdEtn 16:0/20:6, PtdEtn 16:0/22:6, PtdEtn 16:0/24:6, PtdEtn 16:0/26:6, PtdEtn 16:0/28:6, PtdEtn 16:0/30:6, PtdEtn 16:0/32:6, PtdEtn 16:0/34:6, PtdEtn 16:0/36:6, PtdEtn 16:0/38:6, PtdEtn 16:0/40:6, PtdEtn 18:0/20:6, PtdEtn 18:0/22:6, PtdEtn 18:0/24:6, PtdEtn 18:0/26:6, PtdEtn 18:0/28:6, PtdEtn 18:0/30:6, PtdEtn 18:0/32:6, PtdEtn 18:0/34:6, PtdEtn 18:0/36:6, PtdEtn 18:0/38:6, PtdEtn 18:0/40:6, PtdEtn 16:0/18:1, PtdEtn 16:0/18:2, PtdEtn 16:0/18:3, PtdEtn 16:0/20:4, PtdEtn 16:0/22:6, PtdEtn 18:0/18:1, PtdEtn 18:0/18:2, PtdEtn 18:0/18:3, PtdEtn 18:0/20:4, PtdEtn 18:0/22:6, PtdEtn 18:1/18:1, PtdEtn 18:1/18:2, PtdEtn 18:1/18:3, PtdEtn 18:1/20:4, PlsEtn 18:1/22:6 and combinations thereof.

5. The method of claim 4, wherein the human subject is diagnosed with ASD based on a statistically significant ($p<0.05$) increase or decrease in the level of said one or more than one metabolite marker relative to the corresponding data of the reference blood sample from a non-ASD subject.

6. The method of claim 1, wherein the blood samples are analyzed by MS/MS transition.

7. The method of claim 6, wherein the one or more than one metabolite marker is characterized by a MS/MS transition selected from the group consisting of: 718.5/255.2, 746.6/255.2, 774.6/255.2, 802.6/255.2, 830.7/255.2, 858.7/255.2, 886.7/255.2, 914.8/255.2, 942.8/255.2, 970.8/255.2, 998.9/255.2, 1026.9/255.2, 746.6/283.2, 774.6/283.2, 802.6/283.2, 830.7/283.2, 858.7/283.2, 886.7/283.2, 914.8/283.2, 942.8/283.2, 970.8/283.2, 998.9/283.2, 1026.9/283.2, 1054.9/283.2, 716.5/255.2, 744.6/255.2, 772.6/255.2, 800.6/255.2, 828.6/255.2, 856.7/255.2, 884.7/255.2, 912.7/255.2, 940.8//255.2, 968.8/255.2, 996.8/255.2, 1024.9/255.2, 744.6/283.2, 772.6/283.2, 800.6/283.2, 828.6/283.2, 856.7/283.2, 884.7/283.2, 912.7/283.2, 940.8/283.2, 968.8/283.2, 996.8/283.2, 1024.9/283.2, 1052.9/283.2, 714.5/255.2, 742.5/255.2, 770.6/255.2, 798.6/255.2, 826.6/255.2, 854.7/255.2, 882.7/255.2, 910.7/255.2, 938.8/255.2, 966.8/255.2, 994.8/255.2, 1022.9/255.2, 742.5/283.2, 770.6/283.2, 798.6/283.2, 826.6/283.2, 854.7/283.2, 882.7/283.2, 910.7/283.2, 938.8/283.2, 966.8/283.2, 994.8/283.2, 1022.9/283.2, 1050.9/283.2, 712.5/255.2, 740.5/255.2, 768.6/255.2, 796.6/255.2, 824.6/255.2, 852.6/255.2, 880.7/255.2, 908.7/255.2, 936.7/255.2, 964.8/255.2, 992.8/255.2, 1020.8/255.2, 740.5/283.2, 768.6/283.2, 796.6/283.2, 824.6/283.2, 852.6/283.2, 880.7/283.2, 908.7/283.2, 936.7/283.2, 964.8/283.2, 992.8/283.2, 1020.8/283.2, 1048.9/283.2, 738.5/255.2, 766.5/255.2, 794.6/255.2, 822.6/255.2, 850.6/255.2, 878.7/255.2, 906.7/255.2, 934.7/255.2, 962.8/255.2, 990.8/255.2, 1018.8/255.2, 766.5/283.2, 794.6/283.2, 822.6/283.2, 850.6/283.2, 878.7/283.2, 906.7/283.2, 934.7/283.2, 962.8/283.2, 990.8/283.2, 1018.8/283.2, 1046.9/283.2, 736.5/255.2, 764.5/255.2, 792.6/255.2, 820.6/255.2, 848.6/255.2, 876.6/255.2, 904.7/255.2, 932.7/255.2, 960.7/255.2, 988.8/255.2, 1016.8/255.2, 764.5/283.2, 792.6/283.2, 820.6/283.2, 848.6/283.2, 876.6/283.2, 904.7/283.2, 932.7/283.2, 960.7/283.2, 988.8/283.2, 1016.8/283.2, 1044.8/283.2, 734.5/255.2, 762.5/255.2, 790.5/255.2, 818.6/255.2, 846.6/255.2, 874.6/255.2, 902.7/255.2, 930.7/255.2, 958.7/255.2, 986.8/255.2, 1014.8/255.2, 762.5/283.2, 790.5/283.2, 818.6/283.2, 846.6/283.2, 874.6/283.2, 902.7/283.2, 930.7/283.2, 958.7/283.2, 986.8/283.2, 1014.8/283.2, 1042.8/283.2, 700.5/281.2, 698.5/279.2, 696.5/277.2, 722.5/303.2, 746.5/327.2, 728.5/281.2, 726.5/279.2, 724.5/277.2, 750.5/303.2, 774.5/327.2, 726.5/281.2, 724.5/279.2, 722.5/277.2, 748.5/303.2, 772.5/327.2, and combinations thereof.

8. The method of claim 7, wherein the human subject is diagnosed with ASD based on a statistically significant ($p<0.05$) increase or decrease in the level of said one or more than one metabolite marker relative to the corresponding data of the reference blood sample from a non-ASD subject.

9. The method of claim 1, wherein the analytic device or system further comprises a chromatography column, and the blood samples are analyzed by liquid chromatography (LC) and MS/MS transition.

10. The method of claim 1, further comprising:
analyzing at least one blood sample from said subject to obtain quantifying data for one or more than one internal control metabolite; and
obtaining a ratio for each of the levels of said one or more than one metabolite marker to the level obtained for the one or more than one internal control metabolite;
wherein the comparing step (b) comprises comparing each ratio to one or more corresponding ratios obtained for the one or more than one reference blood sample.

11. The method of claim 10, wherein the internal control metabolite is cholic acid.

12. The method of claim 1, wherein the determination of the ASD health state or change in ASD health state comprises the determination of: the presence or absence of ASD, the biochemical ASD phenotype of the subject, an elevated risk of ASD, or a positive, negative, or nil effect of an ASD therapeutic strategy on the subject's underlying biochemical ASD phenotype.

13. The method of claim 12, wherein ASD is detected by measuring any one of the following biochemical ASD phenotypes:
   a) elevated levels of saturated or monounsaturated very long chain fatty acid (VLCFA)-containing ethanolamine phospholipids;
   b) elevated levels of docosahexaenoic acid (22:6, DHA)-containing ethanolamine phospholipids;
   c) elevated levels of polyunsaturated VLCFA-containing ethanolamine phospholipids;
   d) decreased levels of 18:3, 20:3, 22:3, or 24:3-containing ethanolamine phospholipids; and
   e) combinations thereof.

14. The method of claim 1, wherein the blood sample is whole blood, plasma, serum, or a subfraction of whole blood.

15. The method of claim 1, wherein the mass spectrometer of the analytic device or system is selected from the group consisting of: a Fourier transform ion cyclotron resonance, time of flight, orbitrap, quadrupole and triple quadrupole mass spectrometer.

16. The method of claim 1, wherein a liquid/liquid extraction is performed on the blood samples whereby non-polar metabolites are dissolved in an organic solvent and polar metabolites are dissolved in an aqueous solvent.

17. The method of claim 16, wherein the analytic device or system analyzes the extracted samples by positive or negative electrospray ionization, positive or negative atmospheric pressure chemical ionization, or a combination thereof.

18. The method of claim 1, wherein the reference blood sample is taken from a non-ASD subject, one or more ASD subjects not on a therapeutic regimen, or from the human subject at a pre-therapy stage or at an earlier-therapy stage.

* * * * *

UNITED STATES PATENT AND TRADEMARK OFFICE
CERTIFICATE OF CORRECTION

PATENT NO. : 8,273,575 B2  Page 1 of 1
APPLICATION NO. : 12/670426
DATED : September 25, 2012
INVENTOR(S) : Dayan Goodenowe It is certified that error appears in the above-identified patent and that said Letters Patent is hereby corrected as shown below:

In claim 4, at col. 33, line 9, delete "PtdEtn" (each occurrence) and insert --PlsEtn--;
at col. 33, line 10, delete "PtdEtn" (each occurrence) and insert --PlsEtn--;
at col. 33, line 11, delete "PtdEtn" (each occurrence) and insert --PlsEtn--;
at col. 33, line 12, delete "PtdEtn" (each occurrence) and insert --PlsEtn--; and
at col. 33, line 13, delete "PtdEtn" (each occurrence) and insert --PlsEtn--.

Signed and Sealed this
Seventh Day of May, 2013

Teresa Stanek Rea
*Acting Director of the United States Patent and Trademark Office*